US012788577B2

(12) United States Patent
Orr et al.

(10) Patent No.: US 12,788,577 B2
(45) Date of Patent: Nov. 10, 2026

(54) EXPANDABLE COMPLIANT SPINAL FUSION CAGE

(71) Applicant: Brigham Young University (BYU), Provo, UT (US)

(72) Inventors: Daniel Orr, Springville, UT (US); Ronald Alek Sperry, Provo, UT (US); James Anderson, Provo, UT (US); Christian Payne, Provo, UT (US); Brandon Sargent, Provo, UT (US); Anton E. Bowden, Lindon, UT (US); Larry Howell, Orem, UT (US); Michael Bruce Frankel, Mount Pleasant, SC (US)

(73) Assignee: Brigham Young University (BYU), Provo, UT (US)

( * ) Notice: Subject to any disclaimer, the term of this patent is extended or adjusted under 35 U.S.C. 154(b) by 0 days.

(21) Appl. No.: 18/870,043

(22) PCT Filed: Dec. 12, 2022

(86) PCT No.: PCT/US2022/081366
§ 371 (c)(1),
(2) Date: Nov. 27, 2024

(87) PCT Pub. No.: WO2023/114718
PCT Pub. Date: Jun. 22, 2023

(65) Prior Publication Data

US 2025/0331996 A1 Oct. 30, 2025

Related U.S. Application Data

(60) Provisional application No. 63/365,593, filed on May 31, 2022.

(51) Int. Cl.
*A61F 2/44* (2006.01)
*A61F 2/46* (2006.01)
*A61F 2/30* (2006.01)

(52) U.S. Cl.
CPC ............ *A61F 2/447* (2013.01); *A61F 2/4611* (2013.01); *A61F 2002/30322* (2013.01); (Continued)

(58) Field of Classification Search
CPC ........................................................ A61F 2/44
See application file for complete search history.

(56) References Cited

U.S. PATENT DOCUMENTS 6,641,614 B1 * 11/2003 Wagner ................. A61F 2/4455 623/17.15
6,723,126 B1 * 4/2004 Berry .................... A61F 2/4455 606/247

(Continued)

OTHER PUBLICATIONS

International Search Report and Written Opinion for PCT Application No. PCT/US2022/081366, mailed on Jul. 21, 2023, 11 pages.

(Continued)

*Primary Examiner* — David W Bates
(74) *Attorney, Agent, or Firm* — Brake Hughes Bellermann LLP

(57) ABSTRACT

Compliant connectors can span gaps between support segments of an expandable implantable spinal device. The compliant connectors can lay flat when under strain in a stowed position and can expand to maintain an expanded configuration defined by the plurality of support segments when released. A minimally compact size and/or profile of the expandable implantable device may be achieved. which also achieving a relatively large size in the deployed configuration of the device.

22 Claims, 32 Drawing Sheets

(52) U.S. Cl.
CPC ............... *A61F 2002/30331* (2013.01); *A61F 2002/30411* (2013.01); *A61F 2002/30471* (2013.01); *A61F 2002/30494* (2013.01); *A61F 2002/30538* (2013.01); *A61F 2002/30556* (2013.01); *A61F 2230/0091* (2013.01)

(56) References Cited

U.S. PATENT DOCUMENTS

| | | | | |
|---|---|---|---|---|
| 7,628,814 | B2 * | 12/2009 | Studer | A61F 2/4425 623/17.13 |
| 8,043,376 | B2 * | 10/2011 | Falahee | A61F 2/4455 623/17.11 |
| 8,137,401 | B2 * | 3/2012 | Stad | A61F 2/442 623/17.11 |
| 8,313,529 | B2 * | 11/2012 | Lechmann | A61F 2/4425 623/17.16 |
| 8,663,332 | B1 | 3/2014 | To et al. | |
| 8,685,095 | B2 * | 4/2014 | Miller | A61F 2/4611 623/17.11 |
| 8,940,048 | B2 * | 1/2015 | Butler | A61F 2/446 623/17.15 |
| 8,986,387 | B1 | 3/2015 | To et al. | |
| 9,060,876 | B1 * | 6/2015 | To | A61F 2/4611 |
| 9,149,366 | B2 * | 10/2015 | Prevost | A61F 2/447 |
| 9,173,686 | B2 * | 11/2015 | Sheffer | A61B 17/7062 |
| 9,186,259 | B2 | 11/2015 | To et al. | |
| 9,333,092 | B2 | 5/2016 | To et al. | |
| 9,402,733 | B1 | 8/2016 | To et al. | |
| 9,439,771 | B2 * | 9/2016 | Packer | A61F 2/447 |
| 9,463,052 | B2 | 10/2016 | Geist | |
| 9,615,935 | B2 * | 4/2017 | Patterson | A61F 2/44 |
| 9,883,953 | B1 * | 2/2018 | To | A61F 2/4455 |
| 9,913,736 | B2 | 3/2018 | To et al. | |
| 9,999,517 | B2 | 6/2018 | To et al. | |
| 10,058,350 | B2 | 8/2018 | Geist | |
| 10,080,592 | B2 | 9/2018 | Geist | |
| 10,105,238 | B2 * | 10/2018 | Koch | A61F 2/4455 |
| 10,149,773 | B2 | 12/2018 | To et al. | |
| 10,383,743 | B2 | 8/2019 | To et al. | |
| 10,485,675 | B2 * | 11/2019 | Sharifi-Mehr | A61F 2/442 |
| 10,507,116 | B2 | 12/2019 | Shoshtaev | |
| 10,561,504 | B2 * | 2/2020 | Padovani | A61B 17/1671 |
| 10,653,443 | B2 | 5/2020 | Geist | |
| 10,687,845 | B2 | 6/2020 | Geist | |
| 10,709,578 | B2 | 7/2020 | Geist | |
| 10,758,368 | B2 | 9/2020 | To et al. | |
| 10,786,366 | B2 | 9/2020 | To et al. | |
| 10,912,653 | B2 | 2/2021 | To et al. | |
| 11,033,401 | B2 | 6/2021 | Shoshtaev | |
| 11,076,968 | B2 | 8/2021 | To et al. | |
| 11,166,826 | B2 * | 11/2021 | Huang | A61F 2/447 |
| 11,173,040 | B2 * | 11/2021 | Abdou | A61F 2/4611 |
| 11,224,522 | B2 * | 1/2022 | To | A61F 2/4455 |
| 11,234,837 | B2 | 2/2022 | To et al. | |
| 11,253,376 | B2 | 2/2022 | To et al. | |
| 11,259,880 | B1 | 3/2022 | Geist | |
| 11,273,053 | B2 | 3/2022 | Geist et al. | |
| 11,285,018 | B2 | 3/2022 | Shoshtaev | |
| 11,291,554 | B1 * | 4/2022 | Prevost | A61F 2/30749 |
| 11,304,821 | B2 * | 4/2022 | Berry | A61F 2/447 |
| 11,331,197 | B2 | 5/2022 | Shoshtaev | |
| 11,344,353 | B2 | 5/2022 | Geist et al. | |
| 11,357,640 | B2 * | 6/2022 | Weiman | A61F 2/4425 |
| 11,399,877 | B2 | 8/2022 | Geist et al. | |
| 11,426,286 | B2 * | 8/2022 | Spetzger | A61F 2/442 |
| 11,452,617 | B2 | 9/2022 | Geist et al. | |
| 11,633,220 | B2 | 4/2023 | Geist et al. | |
| 11,684,484 | B2 | 6/2023 | Shoshtaev | |
| 11,717,415 | B2 | 8/2023 | To et al. | |
| 11,896,491 | B2 * | 2/2024 | Suddaby | A61F 2/441 |
| 12,036,129 | B2 * | 7/2024 | Howell | A61F 2/468 |
| 2001/0032020 | A1 * | 10/2001 | Besselink | A61F 2/4455 623/17.15 |
| 2002/0068977 | A1 | 6/2002 | Jackson | |
| 2008/0183204 | A1 * | 7/2008 | Greenhalgh | A61B 17/8858 606/198 |
| 2008/0281346 | A1 * | 11/2008 | Greenhalgh | A61F 2/4455 606/191 |
| 2011/0093075 | A1 * | 4/2011 | Duplessis | A61F 2/4425 623/17.16 |
| 2012/0209386 | A1 * | 8/2012 | Triplett | A61F 2/4465 623/17.16 |
| 2014/0277492 | A1 | 9/2014 | Wei | |
| 2015/0012098 | A1 * | 1/2015 | Eastlack | A61F 2/447 623/17.15 |
| 2016/0361177 | A1 * | 12/2016 | Biedermann | A61F 2/442 |
| 2017/0231778 | A1 * | 8/2017 | Overes | A61F 2/4425 623/17.16 |
| 2017/0319253 | A1 * | 11/2017 | Hall | A61B 17/8858 |
| 2018/0193164 | A1 * | 7/2018 | Shoshtaev | A61F 2/4425 |
| 2019/0269521 | A1 * | 9/2019 | Shoshtaev | A61F 2/4455 |

OTHER PUBLICATIONS

Ynchausti, Collin , et al., "Deployable Euler Spiral Connectors", Journal of Mechanisms and Robotics; vol. 14;, Apr. 2022, pp. 021003-1 to 021003-12.

* cited by examiner

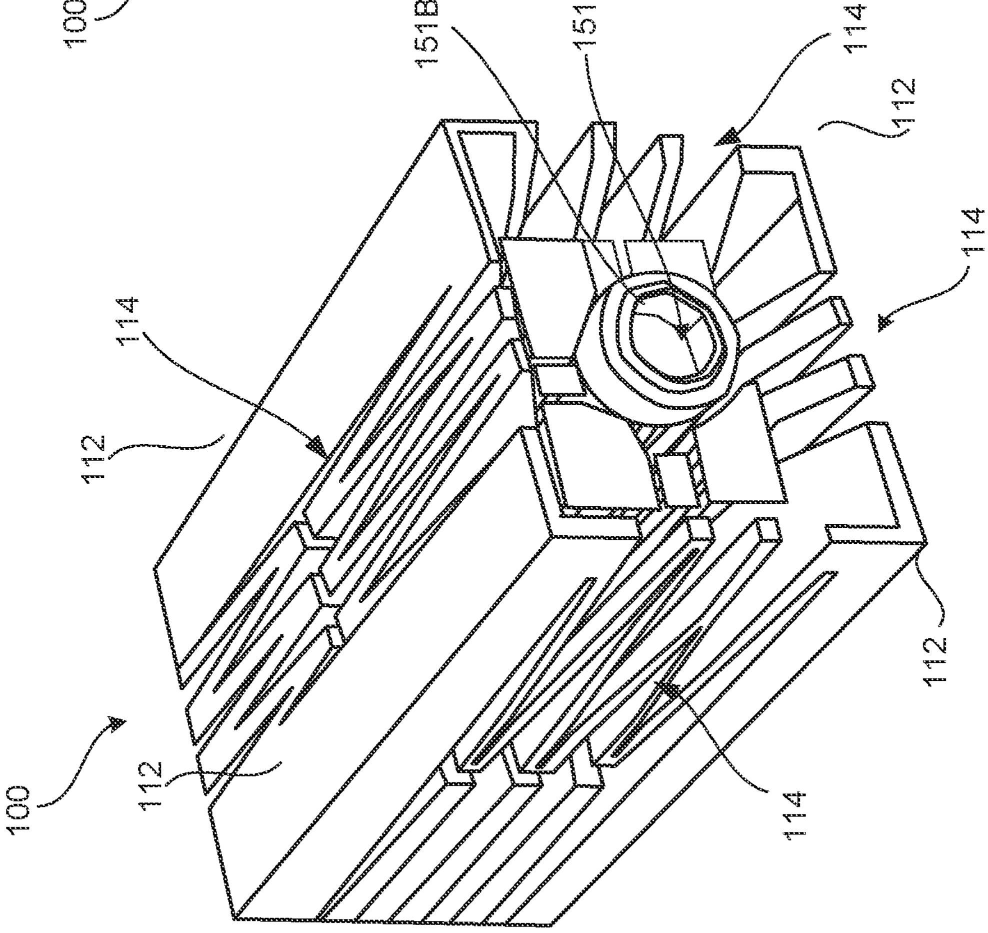
FIG. 1D(1)
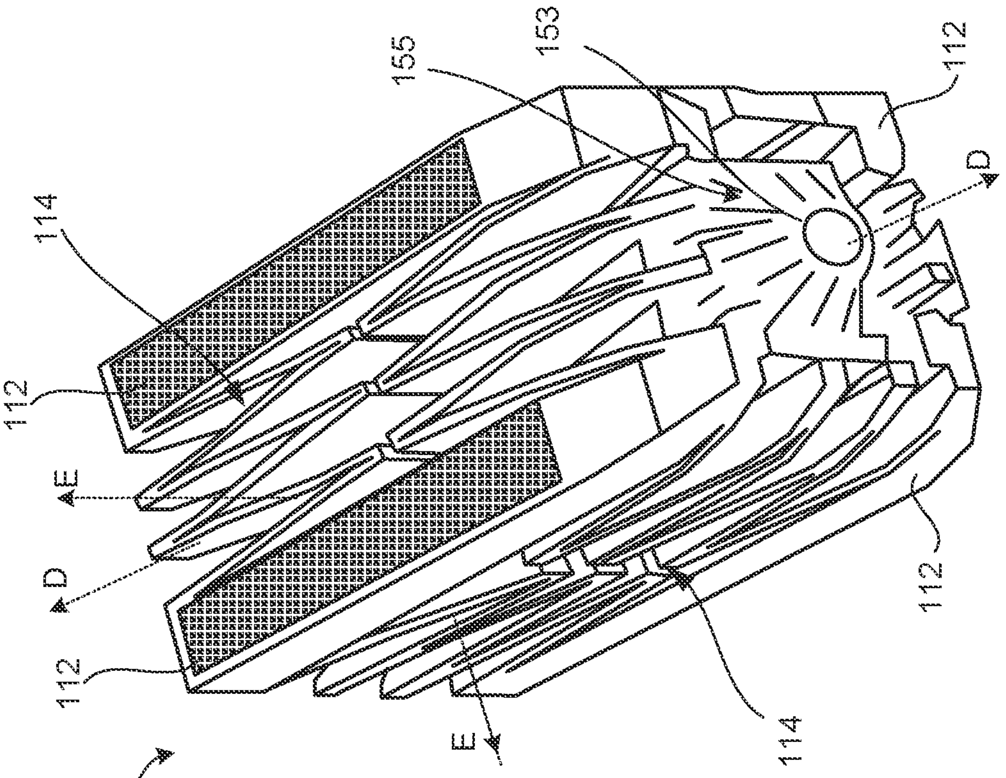
FIG. 1D(2)

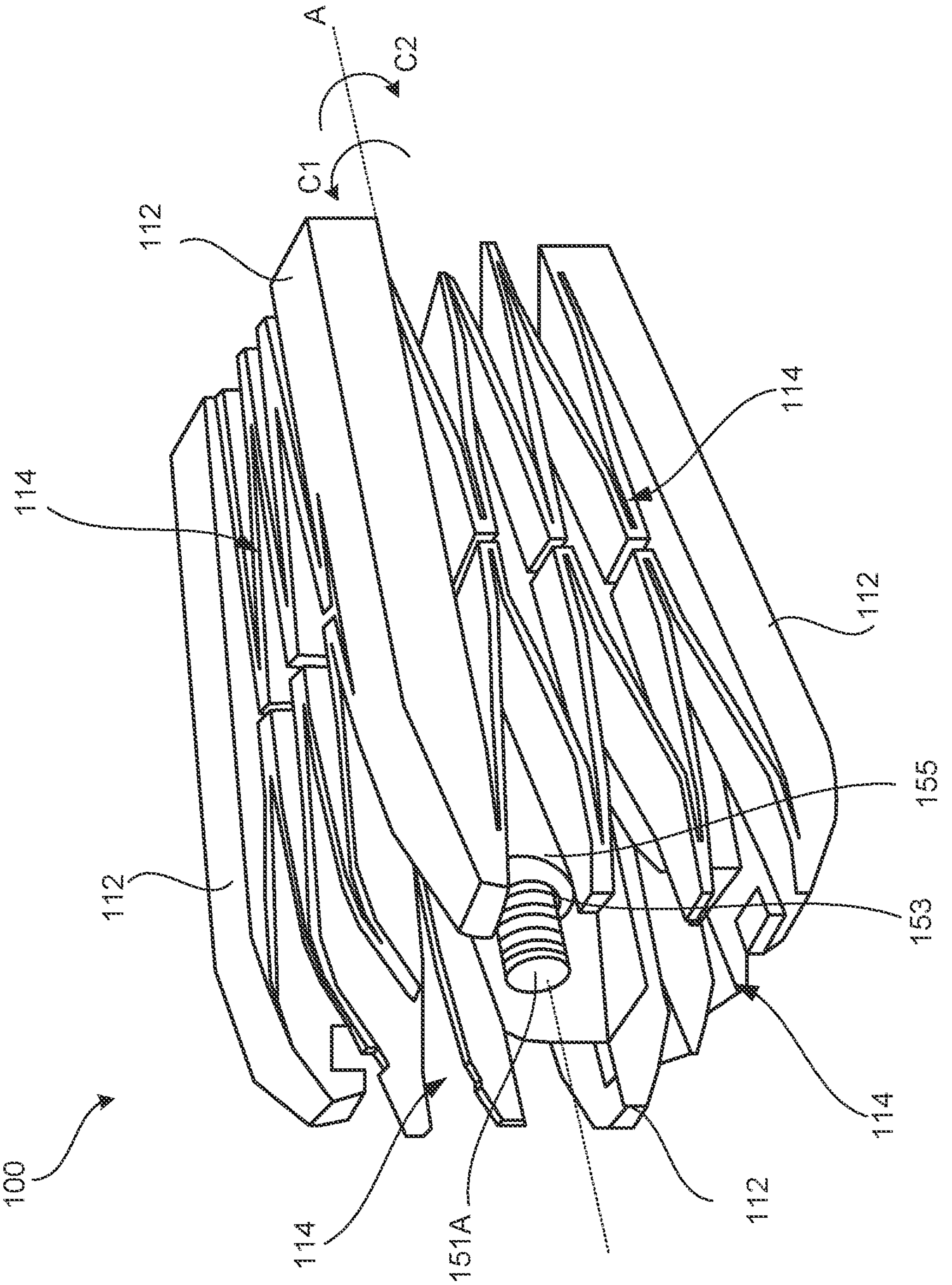
FIG. 1F(1)

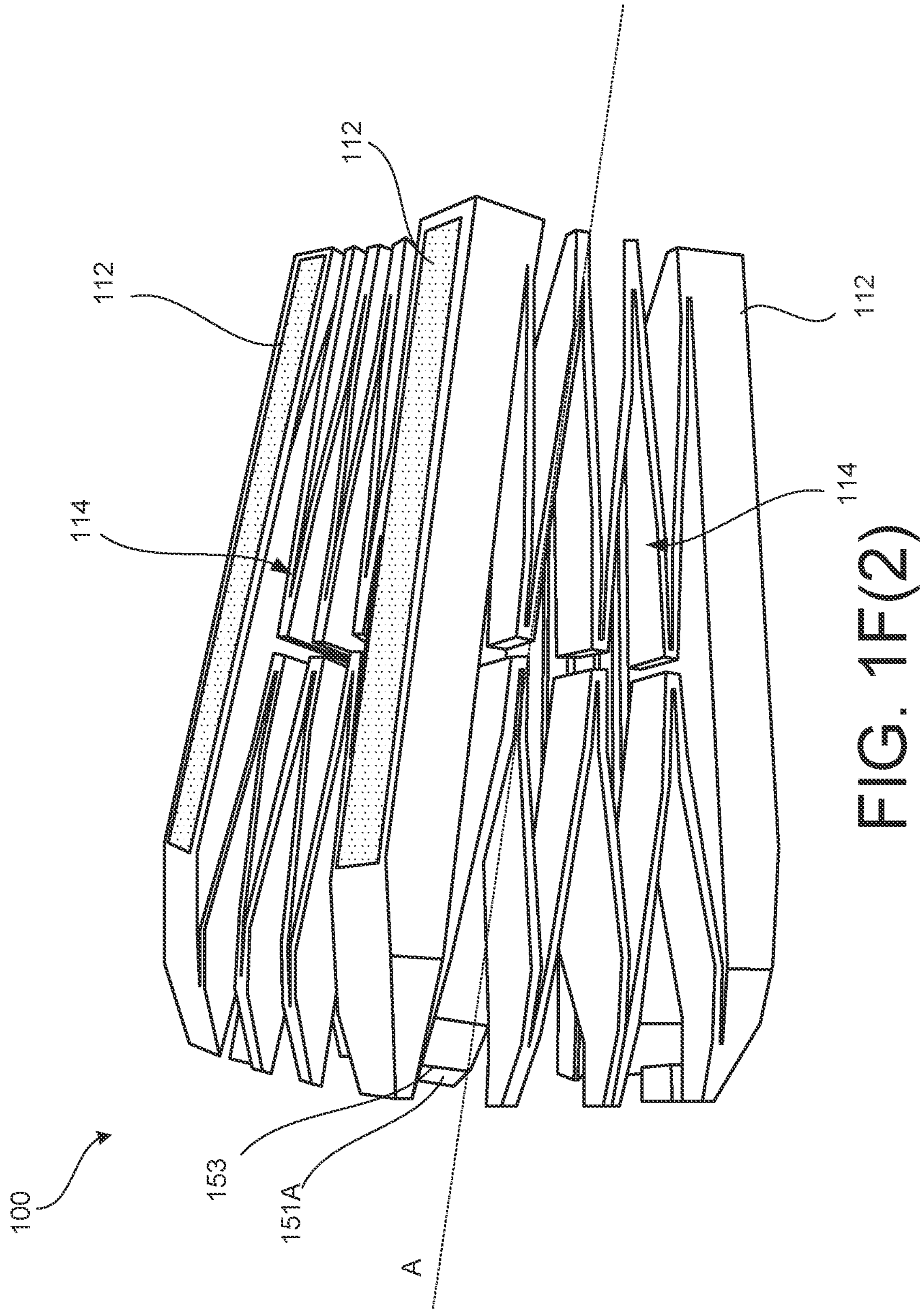
FIG. 1F(2)

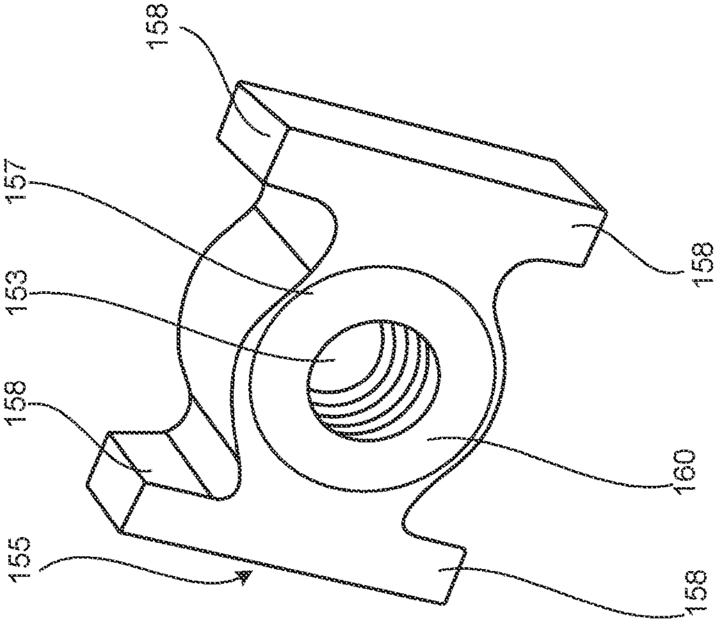
FIG. 3D(2)
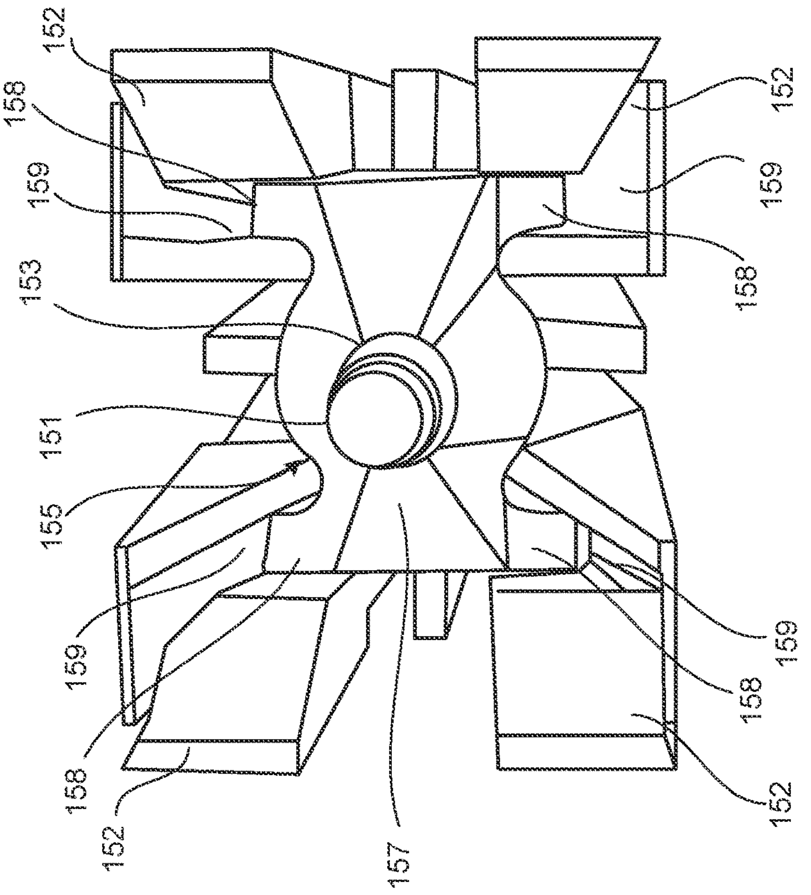
FIG. 3D(1)
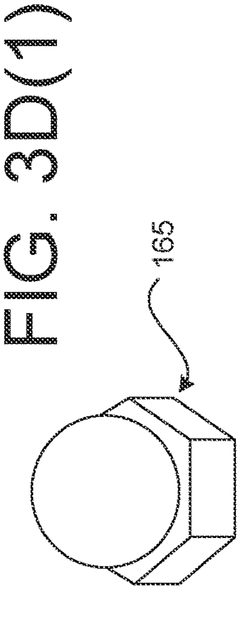
FIG. 3D(3)

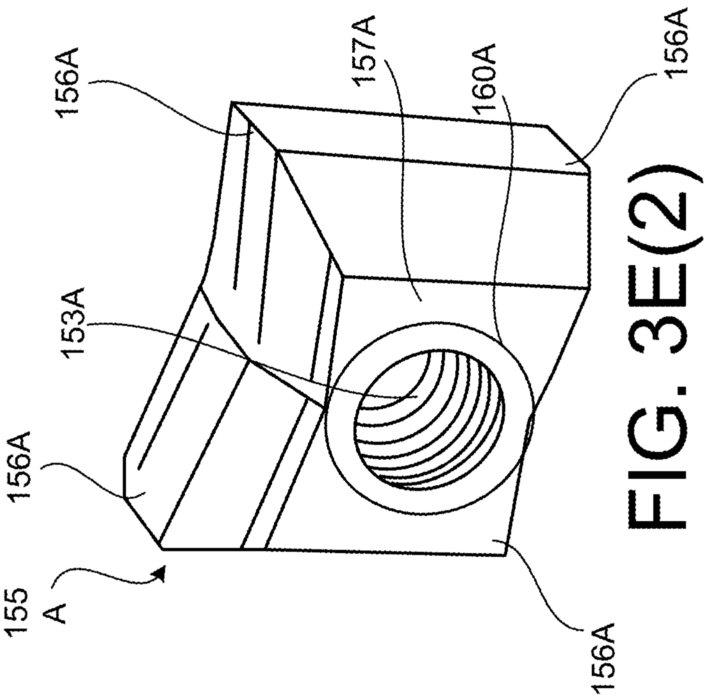
FIG. 3E(2)
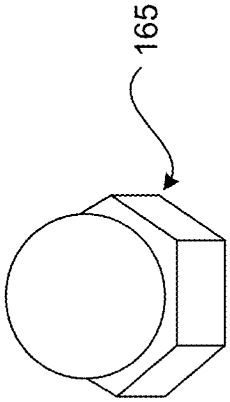
FIG. 3E(3)
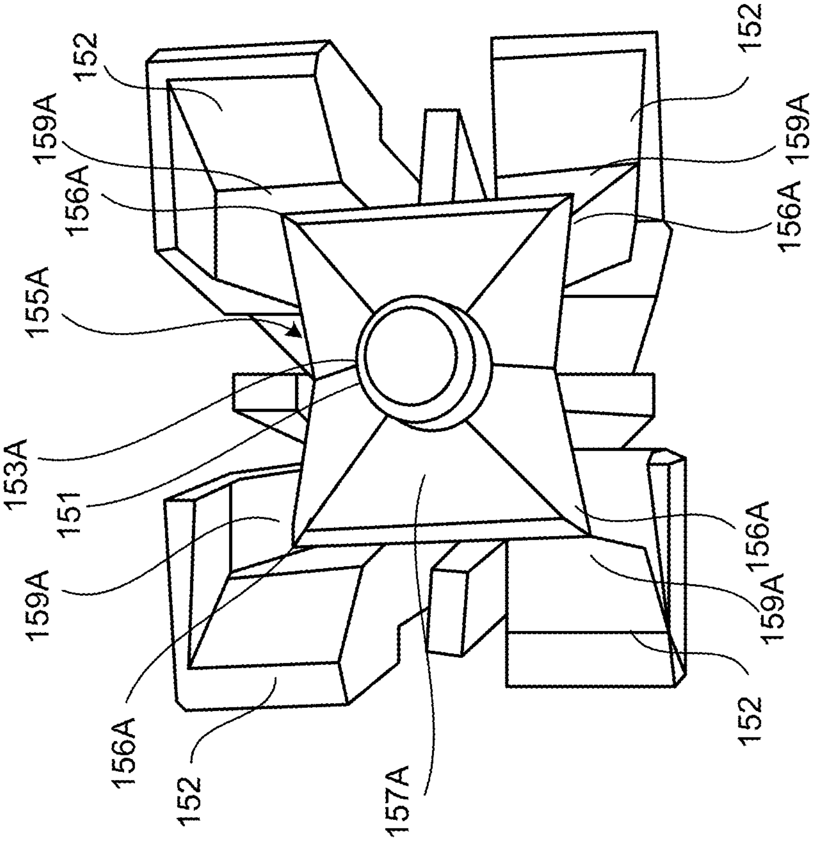
FIG. 3E(1)

EXPANDABLE COMPLIANT SPINAL FUSION CAGE

CROSS-REFERENCE TO RELATED APPLICATIONS

This application is a 35 U.S.C. § 371 National Phase Entry Application from PCT Application No. PCT/US2022/081366, filed on Dec. 12, 2022, entitled "EXPANDABLE COMPLIANT SPINAL FUSION CAGE," and designating the U.S., which claims priority to U.S. Patent Application No. 63/365,593, filed on May 31, 2022, and entitled "EXPANDABLE COMPLIANT SPINAL FUSION CAGE," the disclosures of which are incorporated by reference herein in their entireties.

TECHNICAL FIELD

This description relates, in general, to expandable compliant devices that can be stowed in a compact state and expanded to a larger state, and in particular, to implantable medical devices and equipment that can be stowed in a compact state for placement, and expanded to a larger state.

BACKGROUND

Devices and structures that can be stowed in a compact state and deployed to a larger, expanded state may be desirable in many applications. One area of application of these types of devices is medical equipment. Decreases in the insertion size and/or volume of an implantable device may decrease an incision size for implanting of the device, thus decreasing surgical risk, susceptibility to infection and the like.

SUMMARY

In one general aspect, an implantable device includes a cage portion including a plurality of first support segments, and a plurality of first compliant connectors connecting adjacent first support segments of the plurality of first support segments; an insert portion insertable into an interior space defined by the cage portion; and an actuation device configured to actuate the insert portion, wherein the plurality of first support segments are moved so as to change a configuration of the cage portion in response to actuation of the insert portion.

In some implementations, the insert portion includes a plurality of second support segments; and a plurality of second compliant connectors connecting adjacent second support segments of the plurality of second support segments.

In some implementations, the plurality of first support segments are arranged substantially symmetrically with respect to a central longitudinal axis of the cage portion, the plurality of first support segments are arranged substantially in parallel with respect to the central longitudinal axis of the cage portion in a stowed state of the implantable device, and the plurality of first support segments move radially outward with respect to the central longitudinal axis of the cage portion in response to actuation of the insert portion inserted into the interior space defined in the cage portion.

In some implementations, the actuation device includes a wedge portion positioned at a first end portion of the plurality of second support segments; and a threaded rod having a first end portion thereof threadably engaged with the wedge portion.

In some implementations, the wedge portion includes a body portion; and a plurality of protrusions extending outward from the body portion, and the plurality of second support segments include a plurality of guide grooves formed in an inner surface thereof, at positions corresponding to the plurality of protrusions, wherein the plurality of protrusions are configured to be respectively received in the plurality of guide grooves so as to guide movement of the wedge portion along the threaded rod.

In some implementations, in response to rotation of the threaded rod in a first direction the wedge portion moves on the threaded rod, from the first end portion of the threaded rod toward a second end portion of the threaded rod, and into an interior space defined by the plurality of second support segments of the insert portion; and the plurality of second support segments move outward relative to a central longitudinal axis of the implantable device in response to movement of the wedge portion into the interior space defined by the plurality of second support segments.

In some implementations, in response to initial rotation of the threaded rod in the first direction, the plurality of first support segments and the plurality of second support segments move outward relative to the central longitudinal axis to laterally expand the implantable device; and in response to continued rotation of the threaded rod in the first direction, the plurality of first support segments the plurality of second support segments move outward relative to the central longitudinal axis to vertically expand the implantable device.

In some implementations, the plurality of first support segments of the cage portion move outward relative to the central longitudinal axis of the implantable device in response to the outward movement of the plurality of second support segments of the insert portion.

In some implementations, an amount of expansion of the implantable device at the first end portion of the plurality of first support segments of the cage portion is greater than an amount of expansion of the implantable device at a second end portion of the plurality of first support segments of the cage portion.

In some implementations, an amount of expansion of the implantable device is variable based on a position of the wedge portion on the threaded rod.

In some implementations, the plurality of second support segments are movable relative to each other, and the plurality of first support segments are movable relative to each other in response to movement of the plurality of second support segments, to provide varying amounts of expansion of the implantable device.

In some implementations, the implantable device is expandable between a fully stowed state and a fully expanded state, and wherein the implantable device is expandable to a plurality of intermediate states between the fully stowed state and the fully expanded state.

In some implementations, the implantable device includes an engagement mechanism that selectively engages at least one of the plurality of second support segments with at least one of the plurality of first support segments, the engagement mechanism including a plurality of first detents formed on a mating surface of the at least one of the plurality of first support segments; and a plurality of second detents formed on a mating surface of the at least one of the plurality of second support segments, wherein the plurality of first detents and the plurality of second detents are releasably engageable to maintain a relative position of the at least one of the plurality of first support segments and the at least one of the plurality of second support segments.

In some implementations, in a first mode, in which the insert portion is inserted into the cage portion, the plurality of second support segments move apart in response to actuation of the insert portion, and the plurality of first support members move apart in response to the movement of the plurality of second support segments, to expand the implantable device including the insert portion and the cage portion; and in a second mode, in which the insert portion forms the implantable device, the plurality of second support segments move apart in response to actuation of the insert portion, to expand the implantable device including the insert portion.

In some implementations, at least one of the plurality of first compliant connectors is a Deployable Euler Spiral Connector (DESC), and at least one of the plurality of second compliant connectors is a DESC.

In some implementations, at least one slot is formed in at least one of the plurality of first compliant connectors connecting adjacent first support segments of the cage portion.

In some implementations, texturing is formed on one or more surfaces of one or more of the plurality of first support segments of the cage portion.

In another general aspect, an implantable device includes a plurality of support segments, wherein the plurality of support segments are movable relative to each other, between a stowed configuration and a deployed configuration of the implantable device; a plurality of compliant connectors connecting adjacent support segments of the plurality of support segments, wherein, in the stowed configuration, strain energy is stored in the plurality of compliant connectors; and an actuation device coupled to at least two support segments of the plurality of support segments, wherein the plurality of support segments are configured to move in a first direction in response to release of a holding force that releases the strain energy stored in the plurality of compliant connectors in the stowed configuration of the implantable device, and wherein the plurality of support segments are configured to move in a second direction, toward the deployed configuration, in response to actuation of the actuation device.

In some implementations, the first direction is a lateral direction in which the plurality of support segments move apart from each other in the lateral direction relative to a central longitudinal axis of the implantable device, from the stowed configuration to an intermediate configuration between a fully stowed configuration and a fully deployed configuration, and the second direction is a vertical direction in which the plurality of support segments move apart from each other in the vertical direction relative to the central longitudinal axis of the implantable device from the intermediate configuration toward the fully deployed configuration.

In some implementations, the actuation device includes a rod, including a first end portion pivotably coupled in a first channel formed in a first support segment of the plurality of support segments; and a second end portion movably positioned in a second channel formed in a second support segment of the plurality of support segments, and configured to selectively engage a plurality of teeth formed in the second channel; and an actuation mechanism coupled to the second end portion of the rod, wherein the second end portion of the rod is configured to move in the second channel and selectively engage a plurality of teeth formed in the second channel in response to an external force applied to the actuation mechanism that moves the second end portion of the rod in the second channel, the first end portion of the rod is configured to pivot in response to the movement of the second end portion of the rod in the second channel, and the first support segment and the second support segment are configured to move apart in response to the movement of the second end portion of the rod in the second channel and the pivoting of the first end portion of the rod in the first channel.

In some implementations, the actuation device includes a hinge, including a first arm having a first end portion pivotably coupled to a first support segment of the plurality of support segments; a second arm having a first end portion pivotably coupled to a second support segment of the plurality of support segments, and a pivot portion pivotably coupling a second end portion of the first arm and a second end portion of the second arm; and an actuation mechanism coupled to the pivot portion, wherein, in response to an external force applied to the actuation mechanism that moves the pivot portion from a first vertical position to a second vertical position between the first support segment and the second support segment, the first pivot arm pivots in a first direction relative to the first support segment; the second pivot arm pivots in a second direction relative to the second support segment; and the first support segment and the second support segment move apart in response to the pivoting of the first pivot arm in the first direction and the pivoting of the second pivot arm in the second direction.

In some implementations, the actuation device includes a hinge, including a first arm having a first end portion pivotably coupled to a first support segment and a second support segment of the plurality of support segments; a second arm having a first end portion pivotably coupled to a third support segment and a fourth support segment of the plurality of support segments; and a pivot portion pivotably coupling a second end portion of the first arm and a second end portion of the second arm; and an actuation mechanism coupled to the pivot portion, wherein, in response to an external force applied to the actuation mechanism that moves the pivot portion from a first end portion of the plurality of support segments to an intermediate portion of the plurality of support segments, between the first end portion and a second end portion thereof, the first pivot arm moves in a first channel formed in the first support segment and a second channel formed in the second support segment, from the first end portion to the intermediate portion of the plurality of support segments; the second pivot arm moves in a third channel formed in the third support segment and a fourth channel formed in the fourth support segment, from the first end portion to the intermediate portion of the plurality of support segments; and in response to the movement of the first pivot arm and the second pivot arm, the first support segment and the second support segment move apart, and the third support segment and the fourth support segment move apart.

In some implementations, the actuation device includes a threaded rod positioned between a first support segment and a second support segment of the plurality of support segments; a first shim threadably coupled on a first portion of the threaded rod, the first shim contacting a first inclined surface of one of the first support segment or the second support segment; and a second shim threadably coupled on a second portion of the threaded rod, the first shim contacting a second inclined surface of one of the first support segment or the second support segment, wherein, in response to rotation of the threaded rod, the first shim moves in a first direction along the first portion of the threaded rod, and in the first direction along the first inclined surface; the second shim moves in a second direction along the second portion of the threaded rod, and in the second direction along the second inclined surface; and the first support segment and the second support segment move apart in response to the movement of the first shim along the first inclined surface and the movement of the second shim along the second inclined surface.

The details of one or more implementations are set forth in the accompanying drawings and the description below. Other features will be apparent from the description and drawings, and from the claims.

BRIEF DESCRIPTION OF THE DRAWINGS

FIG. 1D (1) is a first axial end view, and FIG. 1D (2) is a second axial end view, of the stowed state of the example expandable implantable device shown in FIGS. 1A-1C.

FIG. 1F (1) is a perspective view, and FIG. 1F (2) is a side view, of the example expandable implantable device shown in FIGS. 1A-1D (2), illustrating an expanded state of the example expandable implantable device.

FIG. 3D (1) is a plan view of a first side portion of a first configuration of an example wedge portion of the example insert portion shown in FIGS. 3A-3C, inserted into the example insert portion.

FIG. 3D (2) is a perspective view of a second side portion of the example wedge portion shown in FIG. 3D (1).

FIG. 3D (3) illustrates an example nut cap that can be selectively coupled to the example insert portion shown in FIG. 3D (1).

FIG. 3E (1) is a plan view of a first side portion of a second configuration of an example wedge portion of the example insert portion shown in FIGS. 3A-3C, inserted into the example insert portion.

FIG. 3E (2) is a perspective view of a second side portion of the example wedge portion shown in FIG. 3E (1).

FIG. 3E (3) illustrates an example nut cap that can be selectively coupled to the example insert portion shown in FIG. 3E (1).

DETAILED DESCRIPTION

Figure 1A:
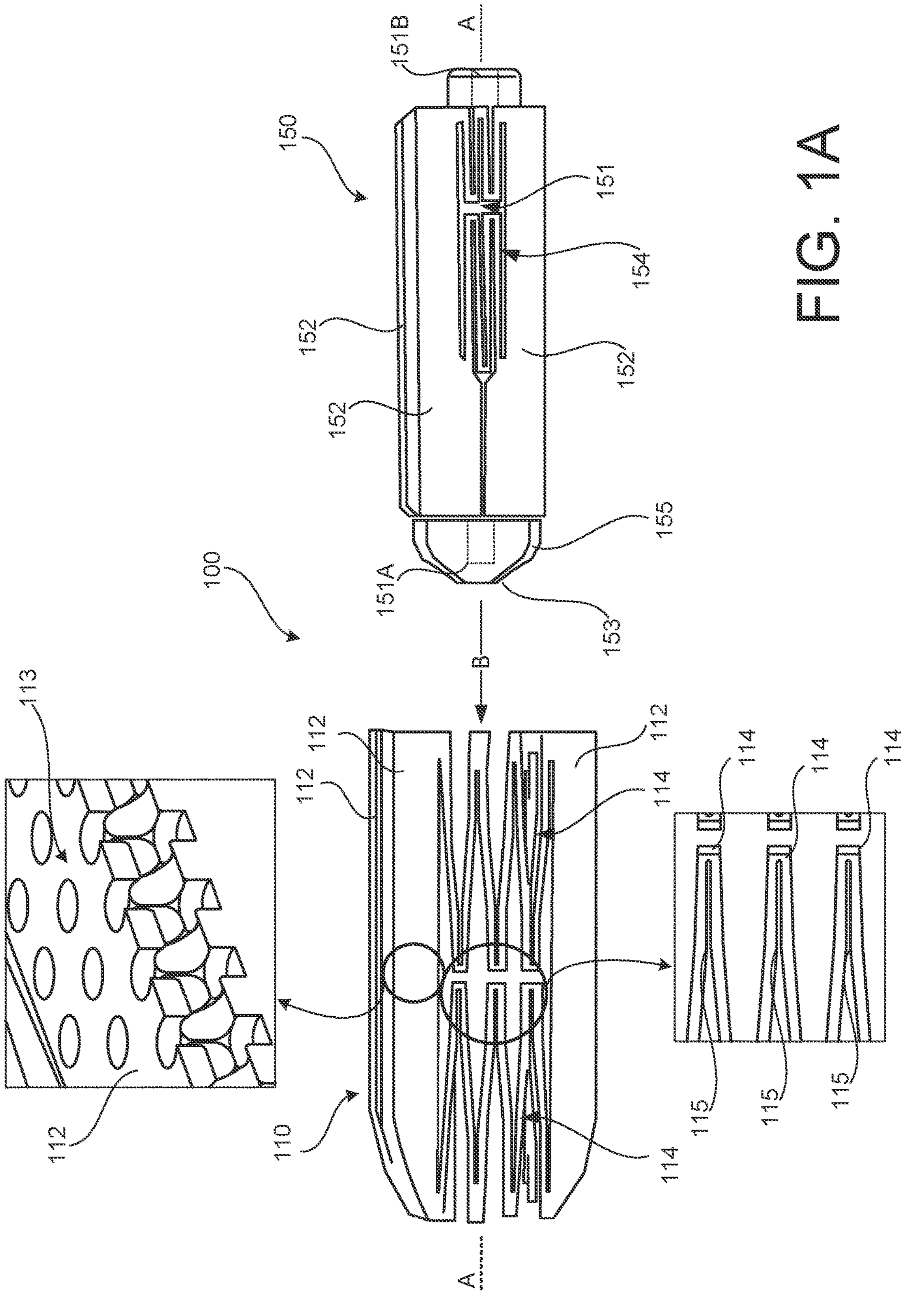
FIG. 1A is a side view.

Minimally invasive surgery (MIS)/minimally invasive surgical procedures have been shown to produce numerous advantages compared to typical open procedures, including, for example, reductions in blood loss, reductions in soft tissue damage, reductions in the length of hospital stays associated with the procedures, and the like. One of the numerous different surgical applications in which MIS procedures provide these types of advantages is in the area of spinal fusion surgical procedures. As MIS fusion surgery continues to evolve, from mini-open approaches, to tubular procedures, to endoscopic procedures, there remains an unmet need for increasingly smaller interbody fusion devices that can be deployed in both the vertical direction and the horizontal direction. Existing spinal fusion cages that fit through a typical surgical approach window may not cover sufficient lateral area to prevent subsidence. Existing spinal fusion cages that fit through the typical surgical approach window may not accommodate the desired range of spinal disc space requirements. Existing spinal fusion cages that fit through the typical surgical approach window may not provide a lordotic angle supportive of the natural spinal curvature. In some examples, a typical surgical approach window may be approximately 7 mm by approximately 9 mm. In some situations, the surgical approach window may be somewhat larger than 7 mm by 9 mm, or somewhat smaller than 7 mm by 9 mm, or differently proportioned. A spinal fusion cage, in accordance with implementations described herein, leverages the benefits of compliant mechanisms to overcome the deficiencies of existing systems.

In general, compliant mechanisms may facilitate the design of devices that can achieve two or more states, including, for example, deployment from a relatively compact stowed state and a relatively larger expanded state. Some forms of compliant mechanisms can sustain relatively large deflections and store strain energy which can be applied for actuation of the device. The strained shape of the compliant mechanisms may be determined at least in part by loads, boundary conditions, material properties, geometry, and other such factors. A configuration (i.e., a shape, a size, and the like) of a device having a relatively compact stowed volume may take into consideration the use of compliant support segments, or compliant members, or compliant connectors, based on the principles of an Euler spiral defined by a curve that exhibits a linear change of curvature along its arc length, and that lie substantially flat when a force is applied at an end portion thereof. Compliant support segments configured based on the Euler spiral may be used to connect rigid support segments such that the rigid support segments can be stowed in a relatively flat manner.

In developing an expandable compliant spinal fusion cage that leverages these qualities of compliant mechanisms, in accordance with implementations described herein, various functional requirements were taken into consideration. These functional requirements include, for example, biocompatibility, ability to deploy significantly both in both a lateral direction and a vertical direction, providing for adjustable lordosis and height, ability to support physiological loads, and simplicity in insertion and deployment. In particular, a structured design process was employed to develop spinal fusion cages that leverage the benefits of the Deployable Euler Spiral Connector (DESC). Gradient based optimization was used to determine the dimensions that achieve the desired strength in the devices without losing compliance. Simulation models were used to analyze stresses in the devices. Due to geometrical and loading symmetry across both the vertical plane and the lateral plane, a quarter of the total model was analyzed. The analysis was performed in three steps. First, the device was displaced to a substantially fully expanded state. Second, a 450 N follower load was applied to the fully expanded device. Finally, a 7.5 Nom moment about the frontal axis was applied to the fully expanded device to simulate flexion. A functional prototype of the device was 3D printed from Ti6Al4V using a laser-sintering process. In some implementations, the device(s) can be made of titanium, polyetheretherketone (PEEK), a metal alloy, a plastic, and other such materials. The functional prototype was inserted and deployed into sawbone models, and into a cadaveric lumbar spine, by a neurosurgeon, to perform initial deployment validation.

Figure 1B:
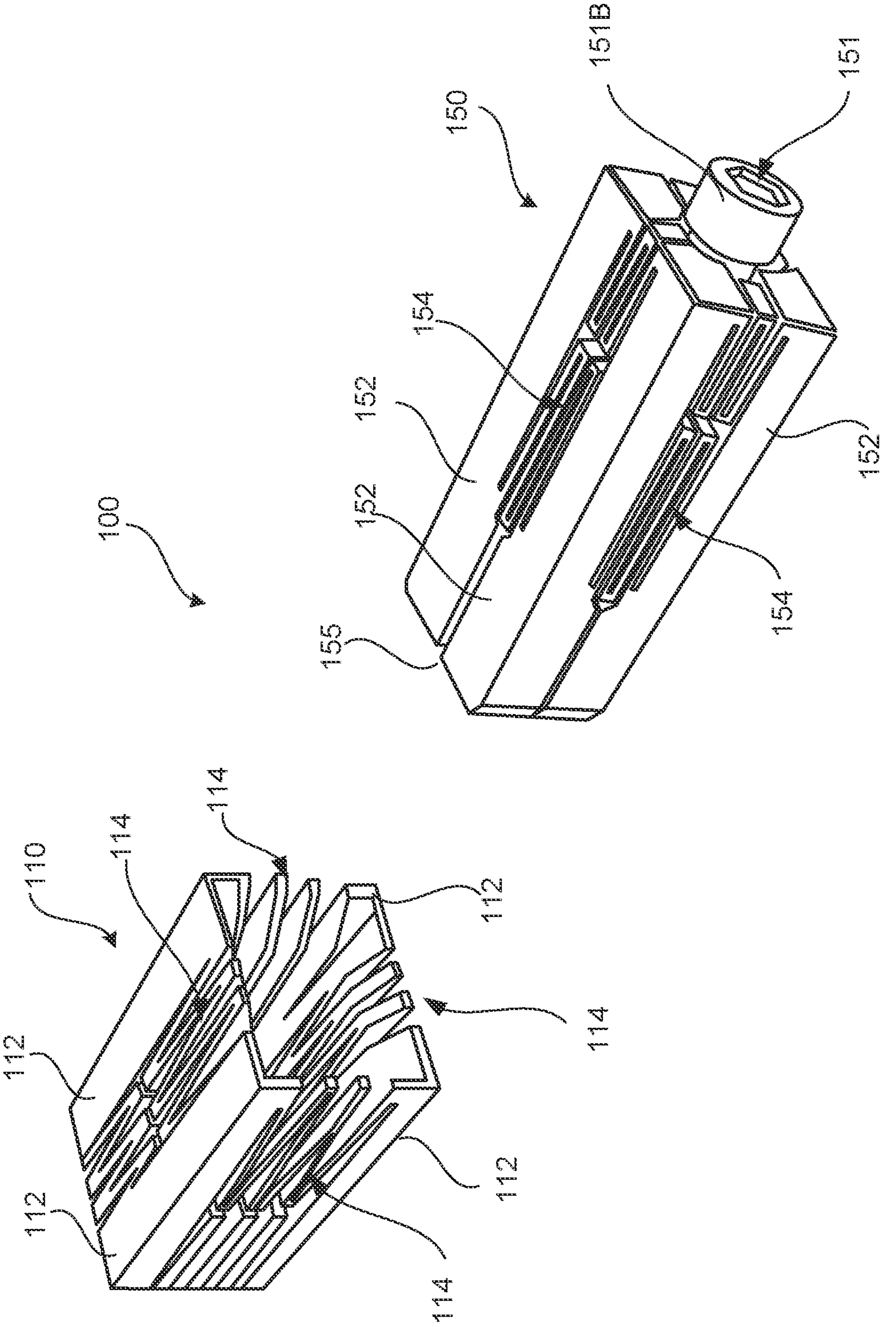
FIG. 1B is a perspective view, of an example expandable implantable device in a decoupled state.
Figure 1C:
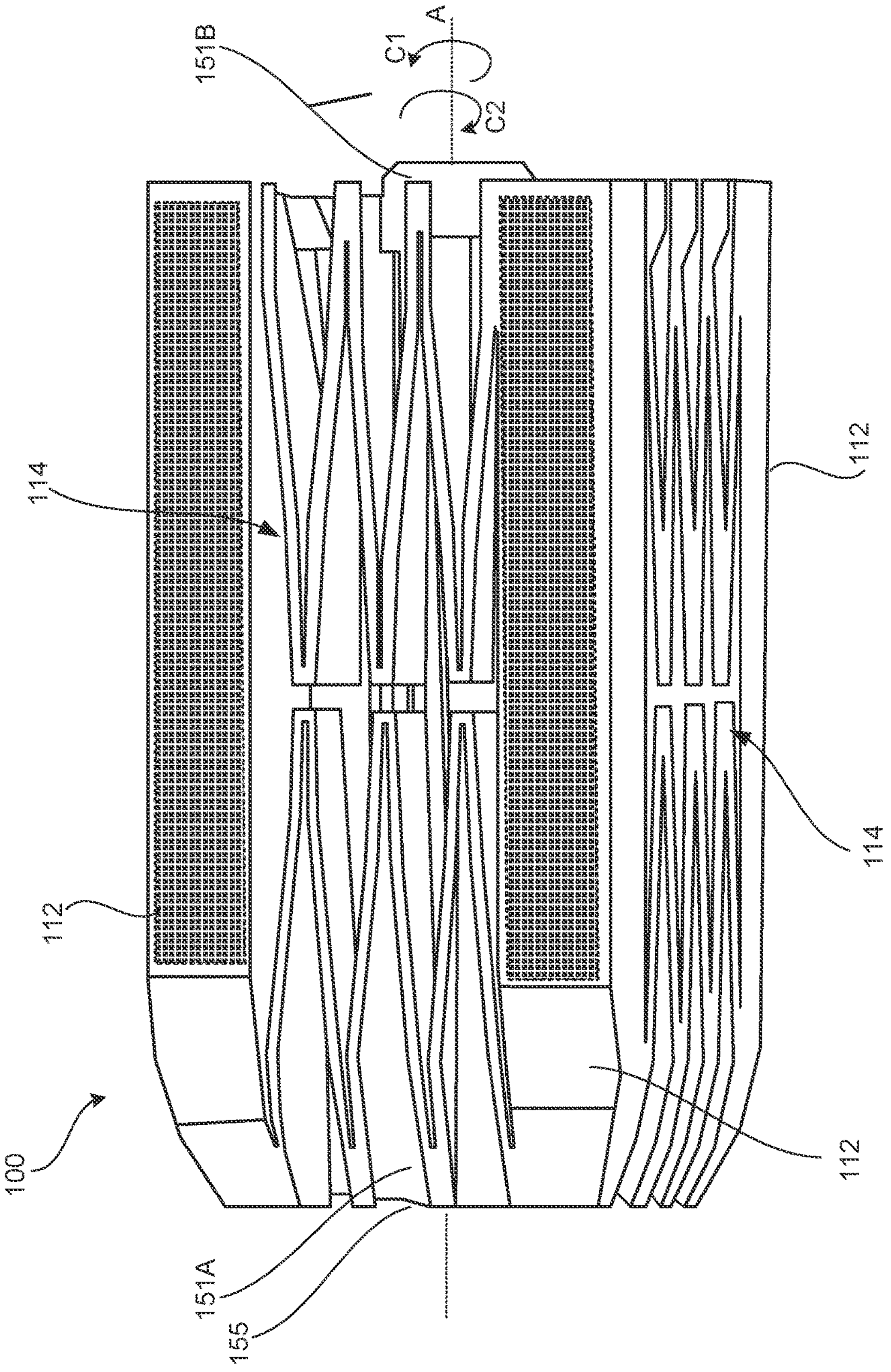
FIG. 1C is a side view of an example insert portion coupled in an example cage portion of the example expandable implantable device shown in FIGS. 1A and 1B, in a stowed state.
Figure 1E:
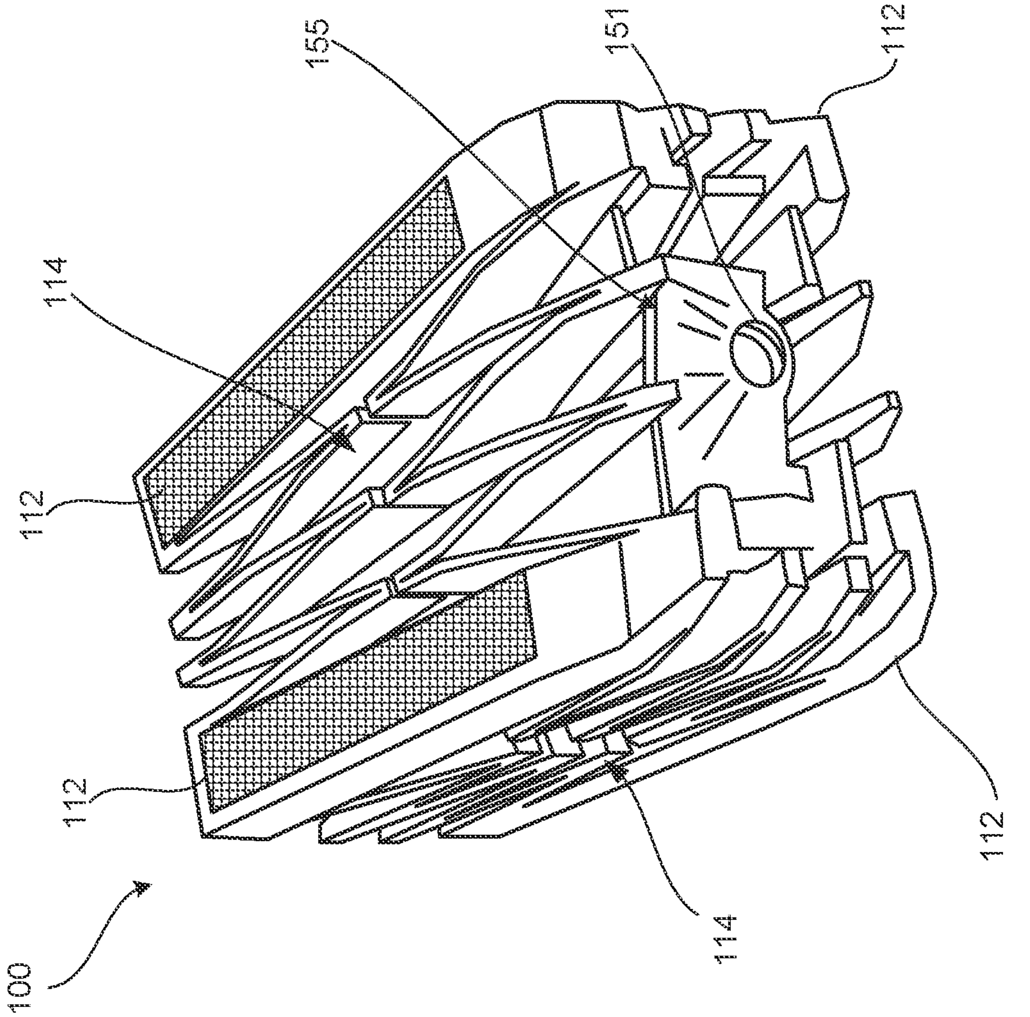
FIG. 1E is a perspective view of the expandable implantable device shown in FIGS. 1A-1D (2), illustrating lateral expansion of the example expandable implantable device.

An example expandable implantable device 100, in accordance with implementations described herein, is shown in FIGS. 1A-1F (2). FIG. 1A is a decoupled side view of an example cage portion 110 and an example insert portion 150 of the example expandable implantable device 100. FIG. 1B is a de-coupled perspective view of the example cage portion 110 and the example insert portion 150 of the example expandable implantable device 100. FIG. 1C is a side view, FIG. 1D (1) is a first axial end view, and FIG. 1D (2) is a second axial end view, illustrating the insert portion 150 coupled in the cage portion 110 of the example expandable implantable device 100. FIG. 1E is a perspective view of the example expandable implantable device 100, illustrating lateral expansion of the example expandable implantable device 100. FIG. 1F (1) is a perspective view, and FIG. 1F (2) is a side view, of an expanded state of the example expandable implantable device 100. In some implementations, the insert portion 150 can be used as an implantable device without the cage portion 110.

Figure 2A:
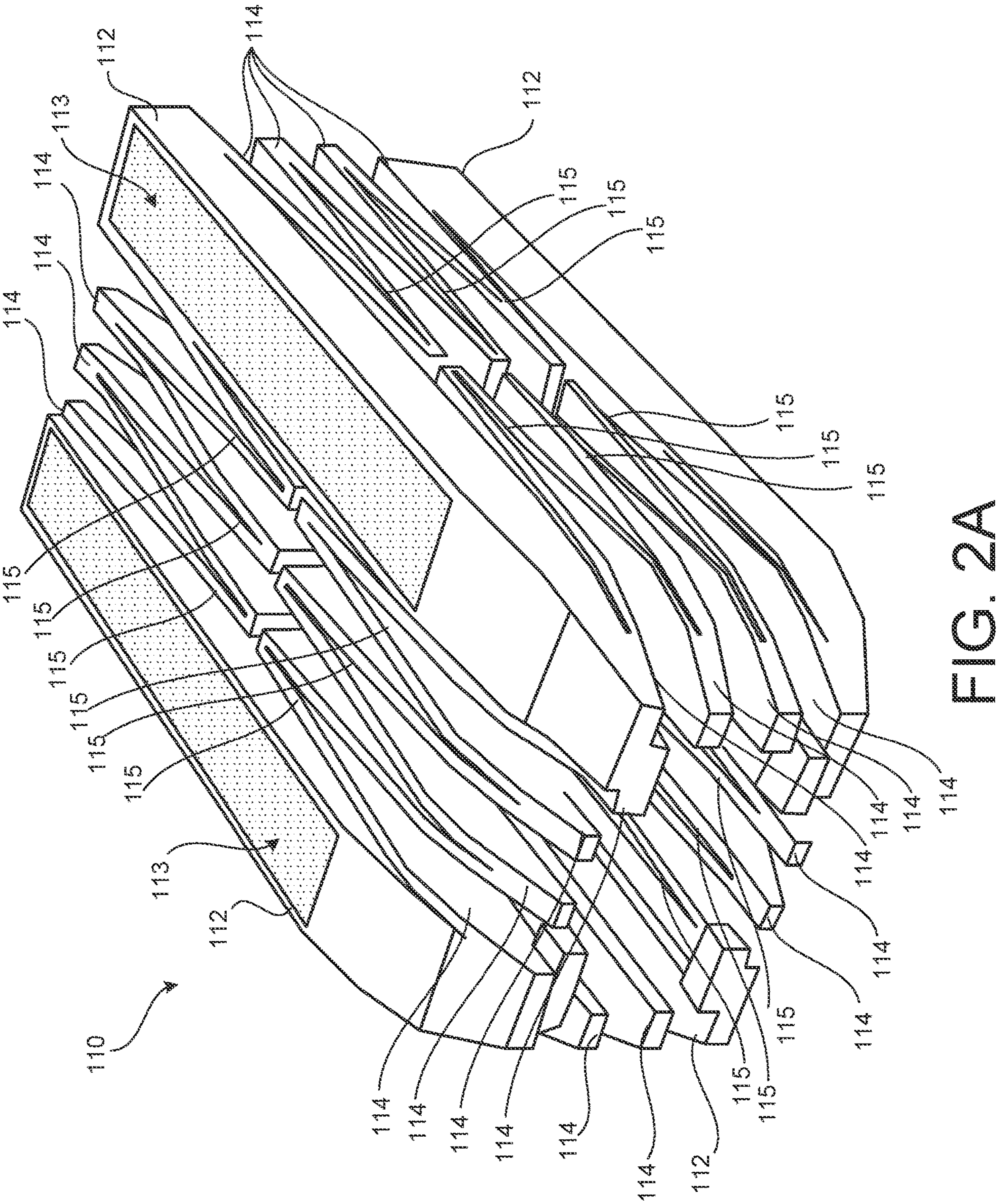
FIG. 2A is a perspective view, of an example cage portion of the example expandable implantable device shown in FIGS. 1A-1F (2).
Figure 2B:
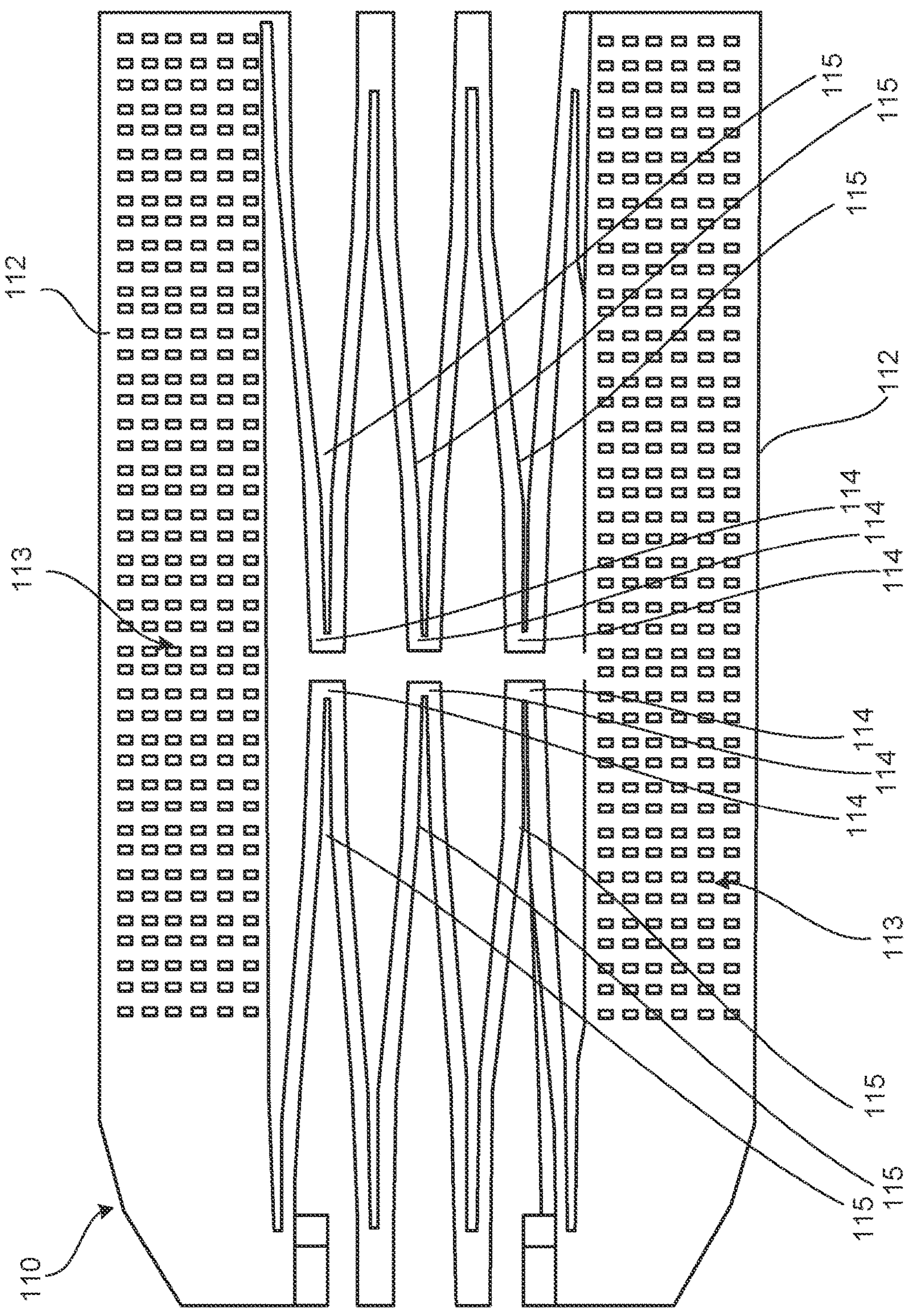
FIG. 2B is a side view.
Figure 2C:
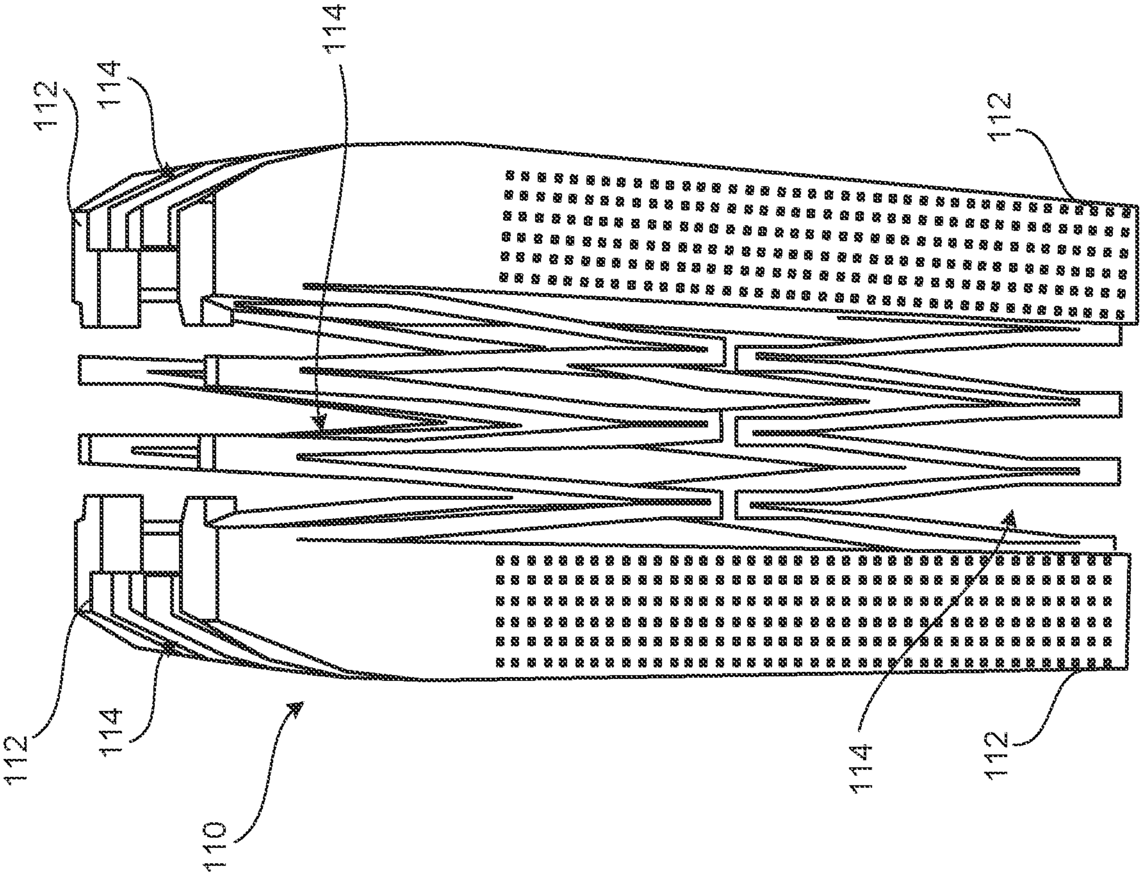
FIG. 2C is an axial end view, of the example cage portion shown in FIG. 2A.

FIG. 2A is a perspective view, FIG. 2B is a side view, and FIG. 2C is an isometric view, of the example cage portion 110 of the example expandable implantable device 100 shown in FIGS. 1A-1F (2).

Figure 3A:
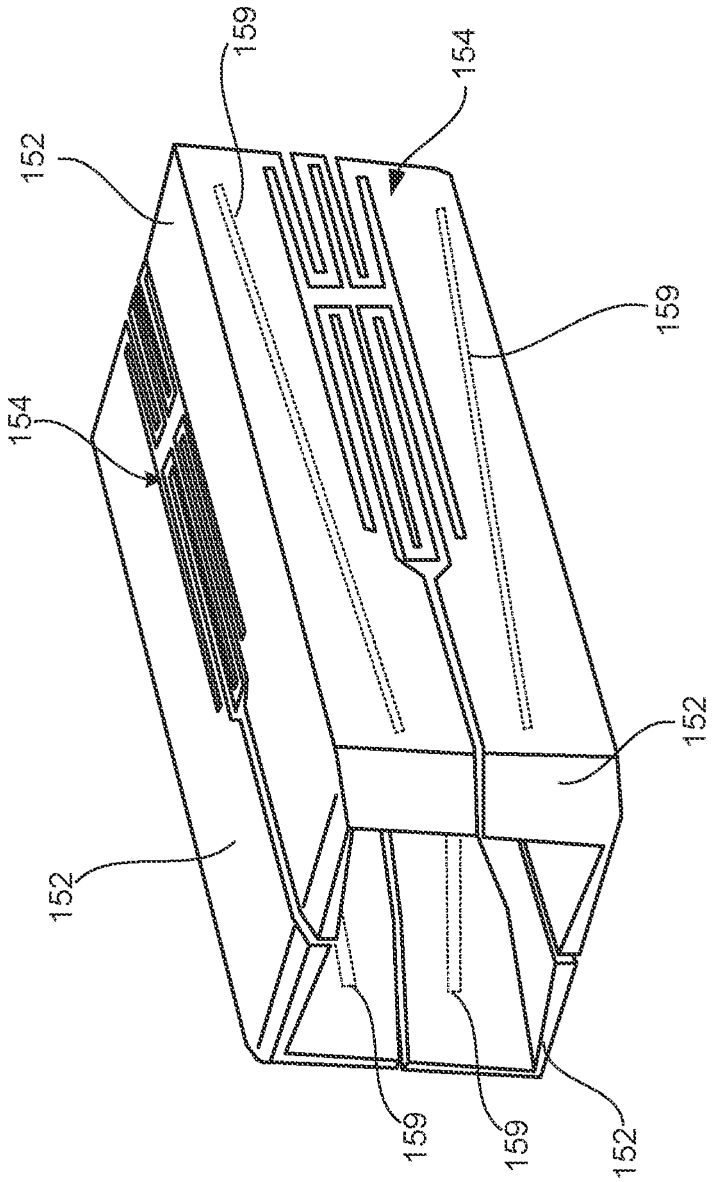
FIG. 3A is a perspective view of an example insert portion of the example expandable implantable device shown in FIGS. 1A-1F (2).
Figure 3B:
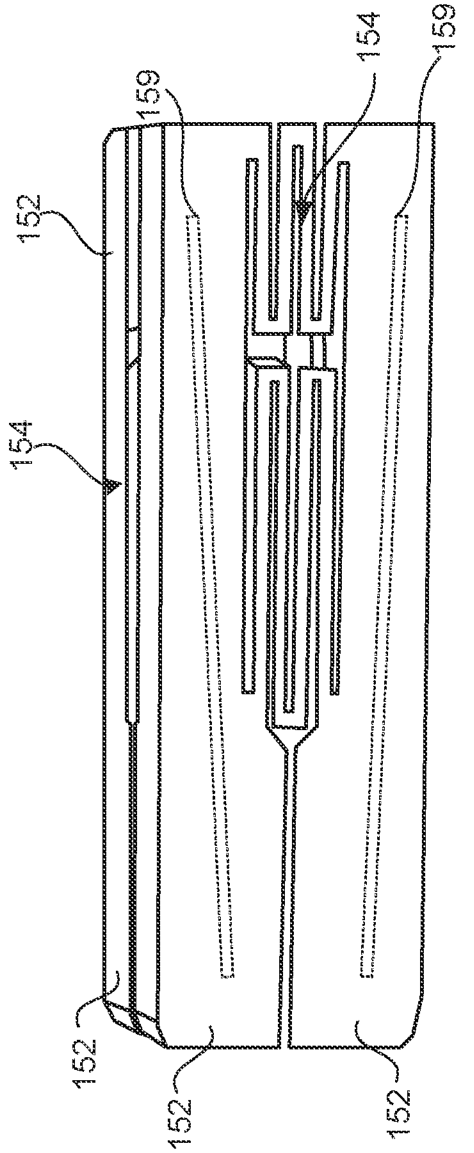
FIG. 3B is a side view.
Figure 3C:
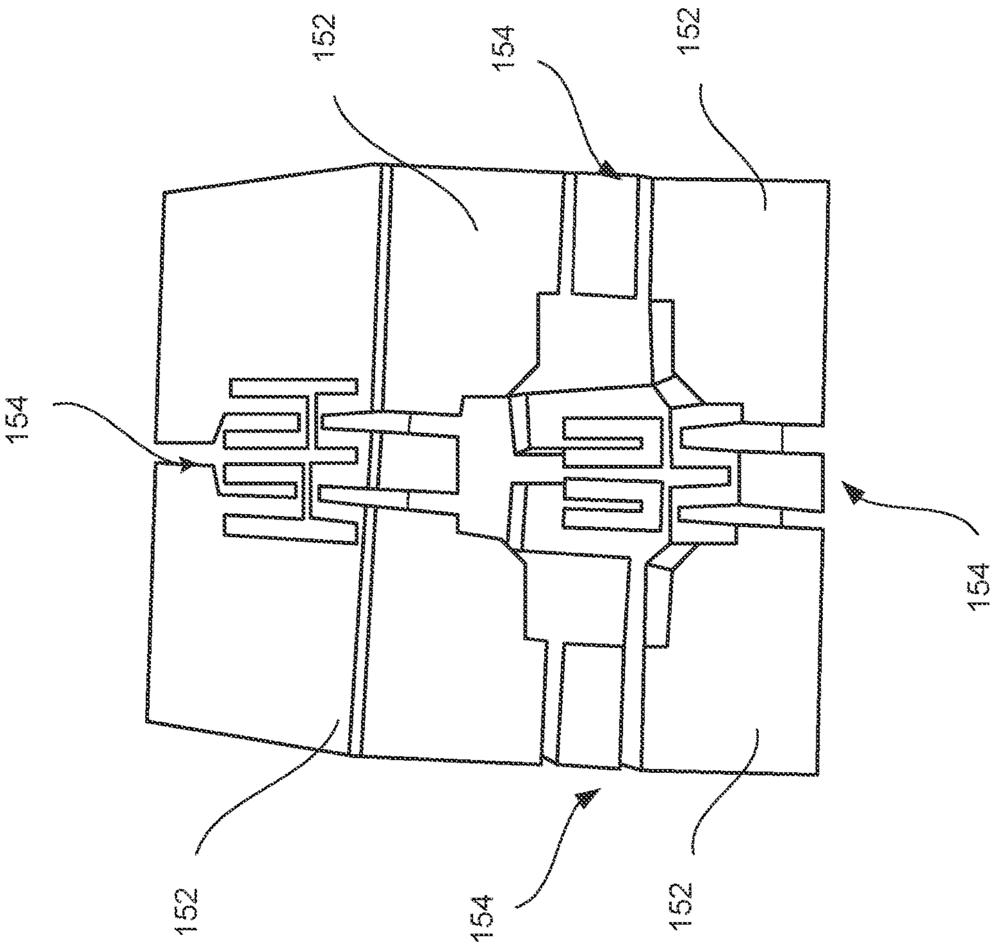
FIG. 3C is an axial end view, of the example insert portion shown in FIG. 3A.
Figure 3F:
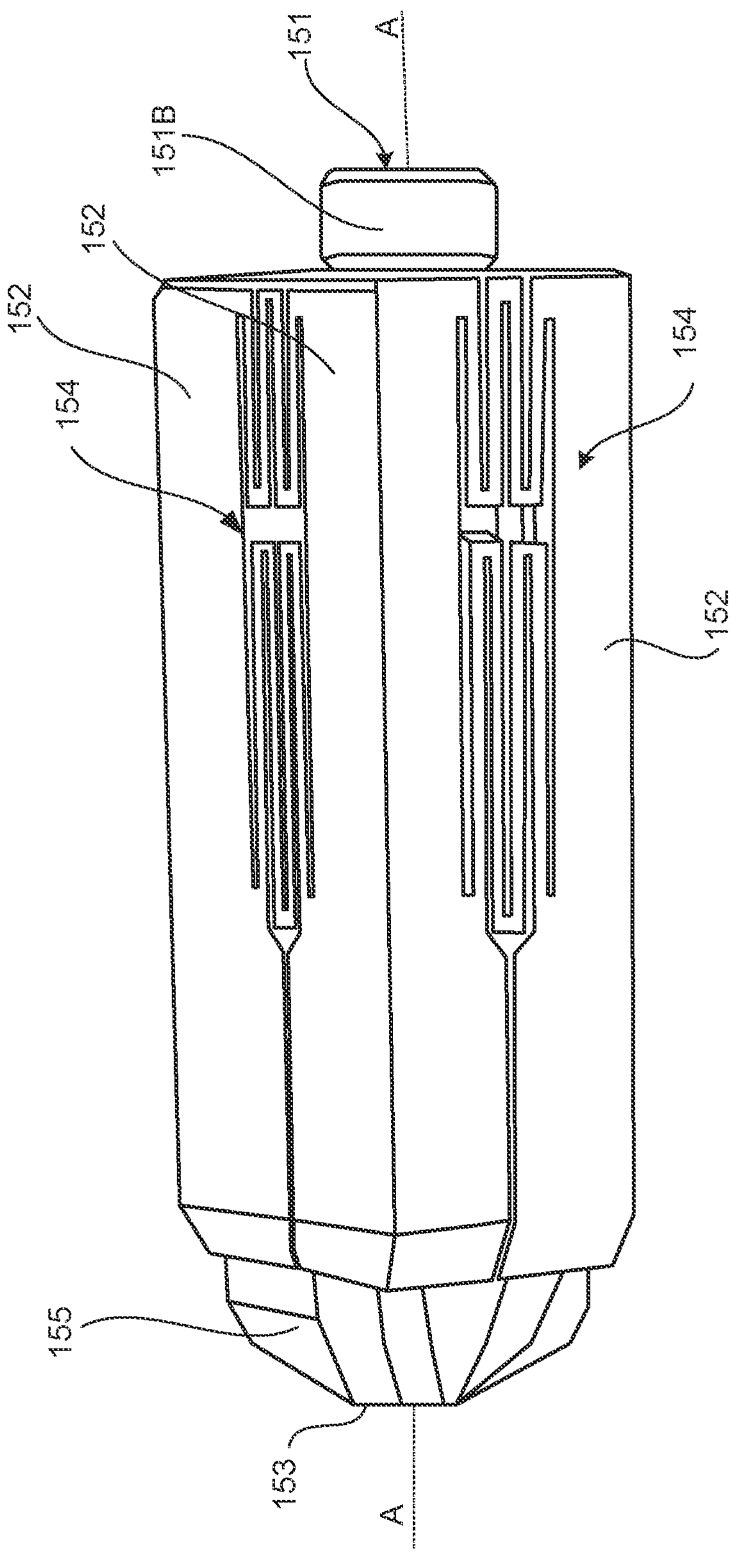
FIG. 3F is a side view of the example insert portion in a stowed state.
Figure 3G:
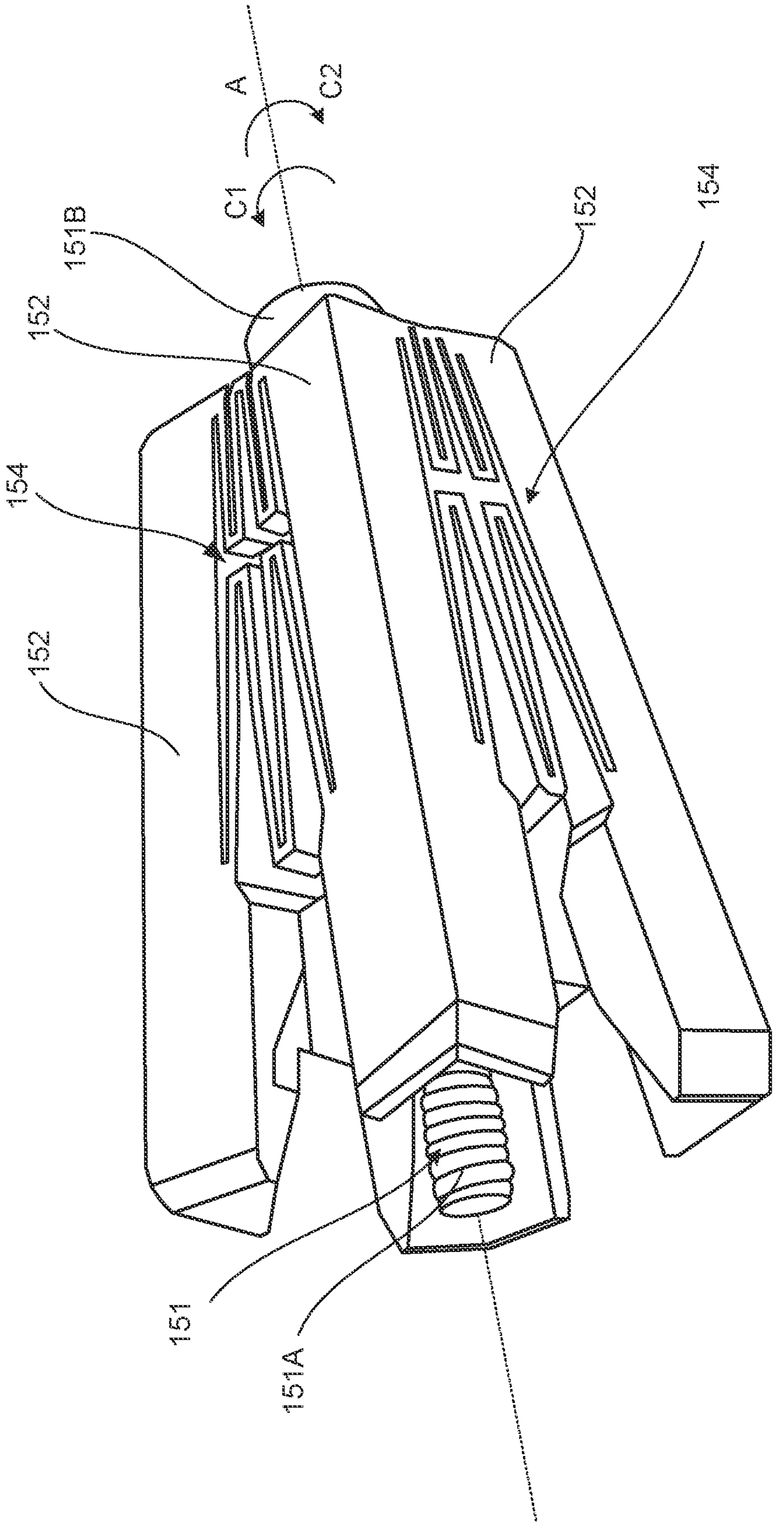
FIG. 3G is a perspective view of the example insert portion in an expanded state.

FIG. 3A is a perspective view, FIG. 3B is a side view, and FIG. 3C is an axial end view, of the example insert portion 150 of the example expandable implantable device 100 shown in FIGS. 1A-1F (2). FIGS. 3D (1) and 3D (2) illustrate a first configuration of the example wedge portion 155 of the example insert portion 150. FIG. 3D (3) illustrates an example nut cap that can be selectively coupled to the threaded rod 151 on which the example wedge portion 155 shown in FIG. 3D (1) is mounted. FIGS. 3E (1) and 3E (2) illustrate a second configuration of the example wedge portion. FIG. 3E (3) illustrates an example nut cap that can be selectively coupled to the threaded rod 151 on which the example wedge portion 155A shown in FIG. 3E (1) is mounted. FIG. 3F is a side view of the example insert portion 150 in a stowed state. FIG. 3G is a perspective view of the example insert portion 150 in an expanded state.

As shown in FIGS. 1A-1F (2) and 2A-2C, the cage portion 110 includes a plurality of support segments 112. The plurality of support segments 112 may be substantially rigid support segments 112 so as to provide for the desired support in the implanted, deployed state of the expandable implantable device 100. Each support segment 112 may be connected to at least one adjacent support segment 112 by at least one compliant connector 114. In the example arrangement shown in FIGS. 1A-1F (2), the support segments 112 are substantially symmetrically arranged about a longitudinal central axis A. In the stowed state, the plurality of support segments 112 are arranged substantially in parallel with respect to the longitudinal central axis A. In the example arrangement shown in FIGS. 1A-1F (2) and 2A-2C, the cage portion 110 includes four rigid support segments 112, simply for purposes of discussion and illustration. The cage portion 110 can include more, or fewer, rigid support segments 112, arranged symmetrically or asymmetrically about the longitudinal central axis A. Similarly, the cage portion 110 can include more, or fewer, compliant connectors 114, arranged similarly to or differently from the arrangement shown in FIGS. 1A-1F (2) and 2A-2C.

As shown in FIGS. 1A-1F (2) and 3A-3G, the insert portion 150 includes a plurality of support segments 152, for example, substantially rigid support segments 152. Each support segment 152 may be connected to at least one adjacent support segment 152 by at least one compliant connector 154. In the example arrangement shown in FIGS. 1A-1F (2) and 3A-3G, the support segments 112 are substantially symmetrically arranged about the longitudinal central axis A. In the example arrangement shown in FIGS. 1A-1F (2) and 3A-3G, the insert portion 150 includes four rigid support segments 152, simply for purposes of discussion and illustration. The insert portion 150 can include more, or fewer, rigid support segments 152, arranged symmetrically or asymmetrically about the longitudinal central axis A. Similarly, the insert portion 150 can include more, or fewer, compliant connectors 154, arranged similarly to or differently from the arrangement shown in FIGS. 1A-1F (2) and 3A-3G.

A wedge portion 155 is positioned at a first end portion of the insert portion 150/first end portion of the plurality of support segments 152. A threaded rod 151 may be positioned within the arrangement of support segments 152 defining the insert portion 150. A first end portion 151A of the threaded rod 151 may be engaged with an opening 153 in the wedge portion 155. The opening 153 may be a threaded opening 153, such that the first end portion 151A of the threaded rod 151 is threadably engaged with the wedge portion 155 via the opening 153. A second end portion of the threaded rod 151 may be accessible at a second end portion of the insert portion 150/second end portion of the plurality of support segments 152. For example, the second end portion 151B of the threaded rod 151 may be accessible to a surgeon, for adjustment of an amount of expansion of the insert portion 150, and a corresponding amount of expansion of the cage portion 110.

In FIGS. 1C-1D (2), the insert portion 150 has been inserted into the cage portion 110, for example in the direction of the arrow B shown in FIG. 1A. In some examples, insertion of the insert portion 150 into the cage portion 110 may represent a first state of the expandable implantable device 100. In some examples, depending on a relative configuration (i.e., a size, a shape, a dimension, an arrangement and the like of the respective support segments

112, 152 and compliant connectors 114, 154), insertion of the insert portion 150 into the cage portion 110 may cause little to no movement of the support segments 112 and compliant connectors 114 of the cage portion 110, i.e., little to no expansion of the cage portion 110 from the stowed state shown in FIGS. 1A and 1B.

In some examples, insertion of the insert portion 150 into the cage portion 110 may cause the support segments 112 of the cage portion 110 to move apart from each other. For example, for some relative configurations of the cage portion 110 and the insert portion 150, insertion of the insert portion 150 into the cage portion 110 may cause the support segments 112 of the cage portion 110 to move outward with respect to the longitudinal central axis A, for example, somewhat radially outward from the longitudinal central axis A. This initial movement of the support segments 112 may in turn cause some amount of expansion of the cage portion 110, with the compliant connectors 114 moving to a corresponding expanded position between the adjacent support segments 112. In some examples, this initial expansion of the cage portion 110 (in response to insertion of the insert portion 150) may represent a first expanded state, or an initial expanded state, of the expandable implantable device 100. In some examples, the expandable implantable device 100 may be further expanded from the first expanded state, or the initial expanded state, to a plurality of further expanded states, in response to manipulation of the threaded rod 151, as shown in FIGS. 1E-1F (2).

In some examples, a configuration of the insert portion 150 relative to the cage portion 110, and an interaction therebetween, for example in response to manipulation of the threaded rod 151, may first cause expansion in a lateral, or horizontal direction, as shown in FIG. 1E. Continued or additional manipulation of the threaded rod 151 may cause further expansion, for example, in a vertical direction, as shown in FIGS. 1F (1) and 1F (2).

In some examples, an amount of expansion, or an amount of displacement of the support segments 112 of the cage portion 110, and a corresponding shape and/or volume defined by the expandable implantable device 100, may be adjusted to accommodate the needs of a particular patient/particular surgical implant procedure. For example, an amount, or a degree, of expansion of the expandable implantable device 100 may be controlled (i.e., increased or decreased) in response to manipulation of the threaded rod 151 within the insert portion 150. That is, rotation of the threaded rod 151 about the central axis A in a first rotational direction corresponding to the arrow C1 may draw the wedge portion 155 into an interior portion of the insert portion 150, i.e., an interior space defined by the support segments 152 and the compliant connectors 154, away from the first end portion 151A of the threaded rod 151, and toward the second end portion 151B of the threaded rod 151.

For example, movement of the wedge portion 155 along the threaded rod 151 in in response to rotation of the threaded rod 151 in the direction of the arrow C1 may cause the insert portion 150 to transition from the stowed state shown in FIG. 3F toward the expanded state shown in FIG. 3G as the wedge portion 155 moves along the threaded rod 151 and pushes the support segments 152 outward, for example, radially outward, with respect to the central axis A. The movement of the support segments 152 of the insert portion 150 in a direction away from the central axis A in turn causes the support segments 112 of the cage portion 110 to also move further apart, thus causing further expansion of the expandable implantable device 100. Similarly, rotation of the threaded rod 151 about the central axis A in a second rotational direction corresponding to the arrow C2 may cause the wedge portion 155 to move along the threaded rod 151 in a direction away from the second end portion 151B and toward the first end portion 151A of the threaded rod 151. Movement of the wedge portion 155 along the threaded rod 151 in this manner may cause the support segments 152 of the insert portion 150 to move toward the central axis A, in turn causing the support segments 112 of the cage portion 110 to also move toward the central axis A, thus reducing an amount of expansion of the expandable implantable device 100.

As noted above, in some examples, the interaction between the wedge portion 155 and the insert portion 150 (for example, in response to manipulation of the threaded rod 151) may cause initial expansion in the lateral, or horizontal direction, as shown in FIG. 1E, with further/continued interaction between the wedge portion 155 and the insert portion 150 (for example, in response to further/continued manipulation of the threaded rod 151) causing expansion in the vertical direction, as shown in FIGS. 1F (1) and 1F (2). In some examples, this initial horizontal, or lateral expansion, followed by vertical expansion, of the expandable implantable device 100 may be facilitated by the interaction of the wedge portion 155 with one or more corresponding guide grooves 159 formed an interior portion of the insert portion 150.

As shown in FIGS. 3E (1) and 3E (2), in some examples, the wedge portion 155 includes a body portion 157 in which the opening 153 is formed. The wedge portion 155 shown in FIGS. 3D (1) and 3D (2) includes protrusions 158 formed at peripheral portions of the body portion 157. The protrusions 158 are configured to be movably, or slidably received in the guide groove 159 of a corresponding support segment 152. Movement of the wedge portion 155 along the threaded rod 151 (in response to manipulation of the threaded rod 151) is guided by the movement of the protrusions 158 received in the guide grooves 159. As shown in FIGS. 3A and 3B, the guide grooves 159 may be configured in a manner that guides expansion of the expandable implantable device 100. For example, the guide grooves 159, and interaction with the protrusions 158, may be configured such that manipulation of the threaded rod 151 initially causes horizontal, or lateral, expansion of the expandable implantable device 100, with continued manipulation of the threaded rod 151 causing vertical expansion of the expandable implantable device 100. In the example shown in FIGS. 3A and 3B, a distance between the guide grooves 159 in adjacent support segments 152 at a first end portion of the adjacent support segments 152 (corresponding to a stowed, or initial expansion state) is less than a distance between the guide grooves 159 at a second end of the adjacent support segments 152 (corresponding to a substantially fully deployed state).

In some examples, a washer 160 may be positioned at an interior facing side of the wedge portion 155. In some examples, the washer 160 may be positioned so as to support a position of the wedge portion 155 on the threaded rod 151. In some examples, a nut cap 165 may be coupled to a distal end portion of the threaded rod 151. In some examples, the nut cap 165 may support a position of the threaded rod 151 in the wedge portion 155. In some examples, the nut cap 165 may provide for support of the wedge portion 155 on the threaded rod 151. In some examples, the nut cap 165 may buttress the wedge portion 155, particularly in response to rotation of the threaded rod 151 in the direction C2, to facilitate a collapsing of the insert portion 150 and/or the cage portion 110 of the expandable implantable device 100.

The ability to substantially fully expand the expandable implantable device 100 in the horizontal, or lateral, direction, prior to expanding the expandable implantable device 100 in the vertical direction, may provide for increased lordotic angle in the placement of the expandable implantable device 100. Full expansion of the expandable implantable device 100 in the horizontal, or lateral direction may spread load over as broad a surface as possible. Full expansion of the expandable implantable device 100 in the horizontal, or lateral direction may provide for engagement with as much cortical bone as possible. The cortical bone at the peripheral portion of the vertebrae is harder than the cancellous bone at the interior portion of the vertebrae. Full, horizontal/lateral expansion of the expandable implantable device 100 may allow a substantial portion of the load to be borne by the harder cortical bone, rather than the cancellous bone, preventing the expandable implantable device 100 from subsiding into the vertebrae, and failing to maintain the desired spacing between the two adjacent vertebrae between which the expandable implantable device 100 is positioned.

FIGS. 3E (1) and 3E (2) illustrate another configuration of an example wedge portion 155A which can be coupled in the insert portion 150 described above. The wedge portion 155A includes a body portion 157A in which an opening 153A is formed to receive the threaded rod 151. Corner portions 156A of the wedge portion 155A shown in FIGS. 3E (1) and 3E (2) formed at peripheral portions of the body portion 157A interact with interior corner portions 159A of a corresponding support segment 152. Movement of the wedge portion 155A along the threaded rod 151 (in response to manipulation of the threaded rod 151) is guided by the movement of the corner portions 156A received in the respective interior corner portions 159A of the support segments 152. In some examples, the interior corner portions 195A of the support segments 152 may be formed so as to interact with the corner portions 156A of the wedge portion 155A so as to guide the movement of the wedge portion 155A similarly to the wedge portion 155 described above with respect to FIGS. 3D (1) and 3D (2).

In some examples, a washer 160 may be positioned at an interior facing side of the wedge portion 155. In some examples, the washer 160 may be positioned so as to support a position of the wedge portion 155A on the threaded rod 151. In some examples, a nut cap 165 as shown in FIG. 3E (3) may be coupled to a distal end portion of the threaded rod 151. In some examples, the nut cap 165 may support a position of the threaded rod 151 in the wedge portion 155A. In some examples, the nut cap 165 may provide for support of the wedge portion 155A on the threaded rod 151. In some examples, the nut cap 165 may buttress the wedge portion 155, particularly in response to rotation of the threaded rod 151 in the direction C2, to facilitate a collapsing of the insert portion 150 and/or the cage portion 110 of the expandable implantable device 100.

Figure 4A:
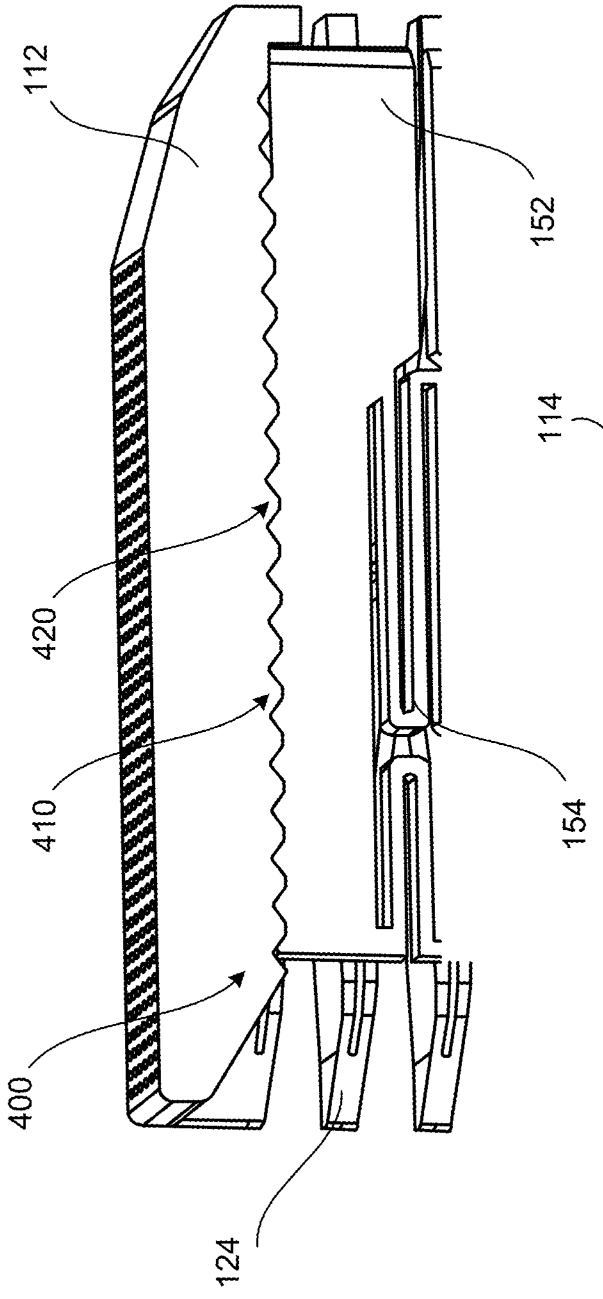
FIG. 4A is a cross-sectional view taken along line D-D of FIG. 1D (2).
Figure 4B:
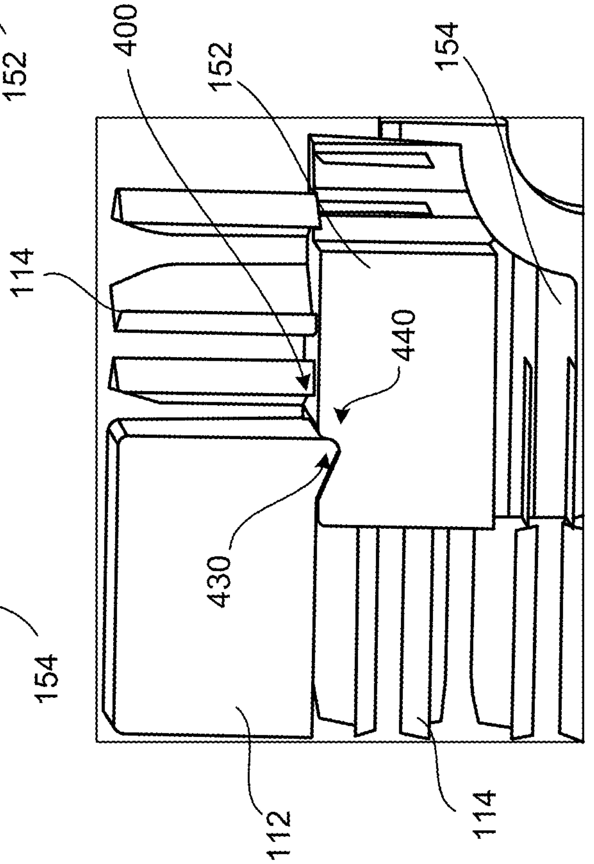
FIG. 4B is a cross-sectional view taken along line E-E of FIG. 1D (2).

In some examples, an engagement mechanism 400 may be provided between mating surfaces of the support segments 112 of the cage portion 110 and the support segments 152 of the insert portion 150. FIG. 4A is a cross-sectional view of the expandable implantable device 100, taken along line D-DF of FIG. 1D (2). FIG. 4B is a cross-sectional view of the expandable implantable device 100, taken along line E-E of FIG. 1D (2). In the example shown in FIGS. 4A and 4B, the engagement mechanism 400 includes a protrusion 430 formed at the mating surface of the support segment 112 of the cage portion 110 is received in a groove 440 formed in the support segment 152 of the insert portion 150. In some examples, the protrusion 430 may be formed on the support segment 152 of the insert portion 150 and the groove 440 may be formed in the support segment 112 of the cage portion 110. Engagement of the protrusion 430 in the groove 440 may provide for lateral stability of the expandable implantable device 100, particularly as the expandable implantable device 100 is expanded beyond the stowed state. In the example shown in FIGS. 4A and 4B, the engagement mechanism 400 includes a plurality of first detents 410 formed on the support segment 112 that selectively engage a plurality of second detents 420 formed on the support segment 152. Engagement of the plurality of first detents 410 and the plurality of second detents 420 may maintain a relative position of the insert portion 150 in the cage portion 110, and between respective support segments 152 of the insert portion 150 and support segments 112 of the cage portion cage portion 110. A pattern or contour of the first detents 410 and the second detents 420 may be complementary, such that the mating surfaces of the support segments 112, 152 can be steadily seated against each other. In some examples, a contour of the plurality of first detents 410 and second detents 420 may be angled so as to facilitate insertion of the insert portion 150 into the cage portion 110. In some examples, engagement between the plurality of first detents 410 and second detents 420 at a first relative position may be released in response to a force applied thereto (for example, in response to rotation of the threaded rod 151 in the direction C2 that causes movement of the insert portion 150 in a direction that collapses the expandable implantable device 100). The plurality of first detents 410 and second detents 420 may be re-engaged at a different relative position, corresponding to a desired degree of expansion of the expandable implantable device 100.

In some examples, slots 115 may be formed in one or more of the compliant connectors 114 of the cage portion 110 of the expandable implantable device 100. The slots 115 may facilitate the expansion of the cage portion 110. The slots 115 are detailed in the inset portion shown in FIG. 1A, and the close in views of the cage portion 110 shown in FIGS. 2A and 2B.

In some examples, one or more surfaces of the support segments 112 of the cage portion 110 of the expandable implantable device 100 may include some form of texturing 113, as shown in the inset portion of FIG. 1A, and also in the close in views of the cage portion 110 shown in FIGS. 2A and 2B. The texturing 113 at one or more surfaces of the support segments 112 may promote the attachment of bone to the expandable implantable device 100 as bone in the area surrounding the expandable implantable device 100 grows and attaches to the textured surfaces.

Figure 5:
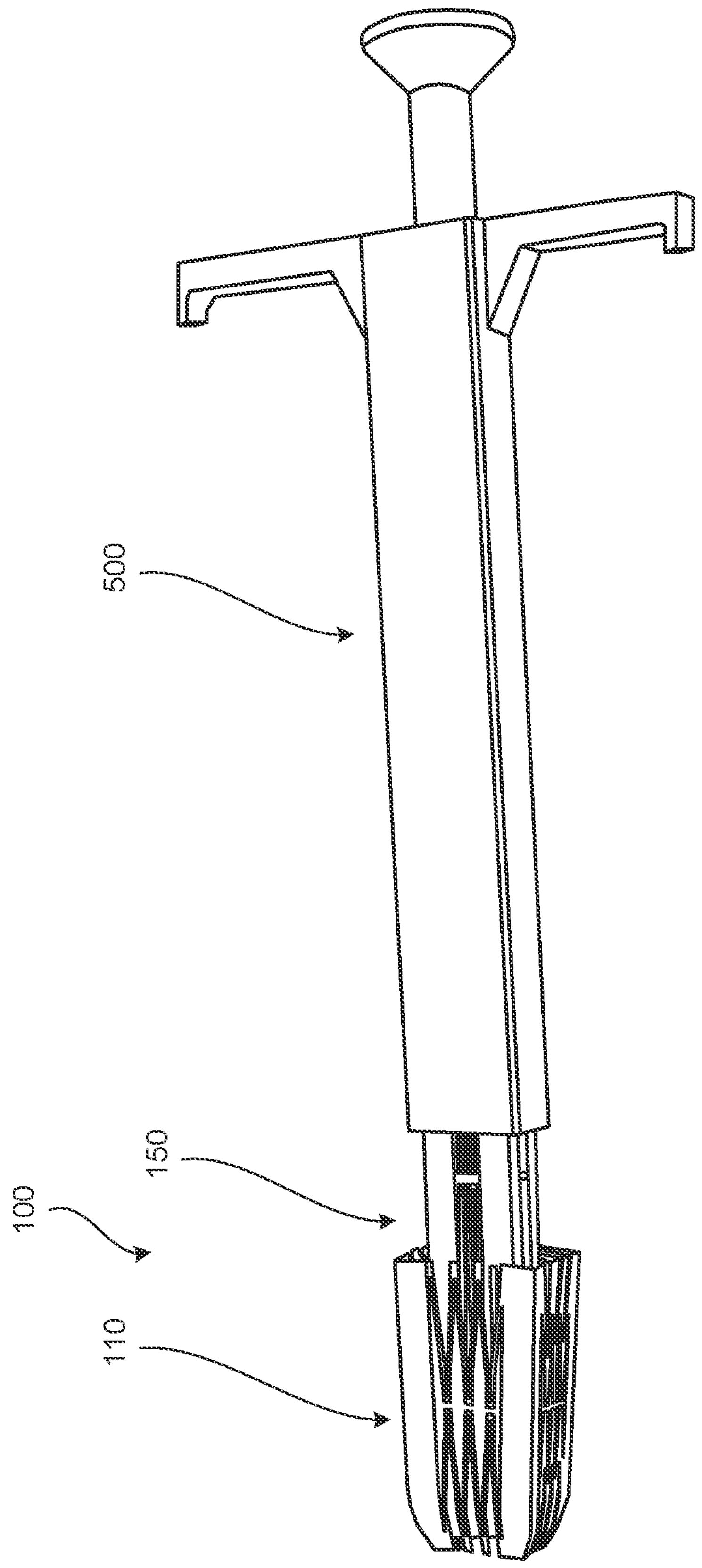
FIG. 5 illustrates an example instrument that is couplable with an expandable implantable device.

FIG. 5 illustrates an example instrument 500 which may facilitate the insertion of the expandable implantable device 100 into a patient. The insert portion 150 of the expandable implantable device 100 may be coupled to an end portion of the instrument 500 for insertion into the cage portion 110. The instrument 500 (for example, an actuation device provided in a handle portion of the instrument 500) may be manipulated to in turn manipulate the threaded rod 151 as described above, to move the insert portion 150 between the stowed state and the expanded state.

In the examples described above, the insert portion 150 is inserted into the cage portion 110, and expanded to, in turn, cause expansion of the cage portion 110. In some examples, the insert portion 150 may be used by itself, without the cage portion 110, with expansion of the insert portion 150 once placed in the patient providing the desired vertebral support. In some examples, the cage portion 110 may be added with the insert portion 150 to provide for an increased, or augmented, volume or size of the expandable implantable device 100.

The advantages provided by the use of DESCs for the compliant connectors 114 of the cage portion 110 and/or the compliant connectors 114 of the insert portion 150 of the expandable implantable device 100 as described above enable a significant increase in post-implantation deployment height expansion of the expandable implantable device 100. For example, in some situations, the expandable implantable device 100 described above may demonstrate an approximately 225% increase in deployment height expansion over comparable devices, making the expandable implantable device 100 applicable for a wide variety of minimally invasive surgical procedures. Additionally, the threaded engagement of the wedge portion 155 on the threaded rod 151 provides for substantially continuously variable adjustment in lordotic angle. In some examples, the substantially continuously variable adjustment in lordotic angle may be from between approximately 0 degrees to approximately 9.8 degrees. In some examples, the substantially continuously variable adjustment in lordotic angle may be greater than 9.8 degrees. The continuously variable adjustment of lordotic angle may further enhance the applicability of the expandable implantable device 100 to a wider variety of minimally invasive surgical procedures.

Thus, an expandable implantable device, in accordance with implementations described herein, may have a relatively compact stowed configuration, and a relatively larger deployed configuration. The relatively compact stowed configuration of the implantable device may facilitate the minimally invasive placement of the implantable device in a patient, with the implantable device being deployable to the larger configuration after placement/implant in the patient. The coupling of the plurality support segments of the cage portion and the plurality of support segments of the insert portion by the compliant connectors may provide for a compact arrangement of the plurality of support segments in the stowed configuration, and for separation of the plurality of support segments to the deployed state. The ability to adjust an amount, or a degree, of expansion of the expandable implantable device through manipulation of the threaded rod and interaction between the wedge portion of the insert portion and the support segments of the cage portion, may further enhance efficacy of the expandable implantable device.

Implantable medical devices, such as spinal implant devices used in spinal fusion procedures, may benefit from the efficient stowing and deployment afforded by the use of compliant connectors, in the form of DESCs as described above. Expandable implantable spinal disc devices may be implanted to maintain disc height and stabilize the spinal column while bone fusion occurs. In some examples, expandable implantable spinal disc devices may also guide bone growth through the implanted device, allowing the bones to fuse.

While it may be desirable to make use of the smallest possible expandable implantable device to enable the smallest possible incision, in some situations the use of a relatively small, or undersized, implantable device can lead to subsidence involving the sinking of the implantable device into the surrounding bone due to differences in mechanical stiffness of the implantable device in comparison with the supporting bone (i.e., stress overload of the bone). An expandable implantable device having a relatively small insertion size/profile, and that is expandable to a larger deployed configuration may provide for smaller incision areas while also providing the necessary support area of contact with cortical bone when implanted. Thus, expandable implantable devices may address the contradictory desires for a relatively smaller incision and a relatively larger implant to provide stability and reduce subsidence.

FIGS. 6A-6E illustrate an example expandable implantable device 600, in accordance with implementations described herein. The example expandable implantable device 600 includes a plurality of support segments 620, for example, substantially rigid support segments 620, with compliant connectors 640 connecting adjacent support segments 620. The example expandable implantable device 600 can include more, or fewer, support segments 620, arranged similarly or differently than shown in FIGS. 6A-6E. In some examples, at least some of the support segments 620 are at least partially hollow. In some examples, components of an actuation device 630 and/or a ratcheting mechanism 650 of the example device 600 may be at least partially accommodated within the hollow portions of the support segments 620 in the stowed state shown in FIG. 6A. The actuation device 630 may provide for at least a portion of the expansion and/or deployment of the example device 600. The ratcheting mechanism 650 may maintain a desired level of expansion of the example device 600.

Figure 6A:
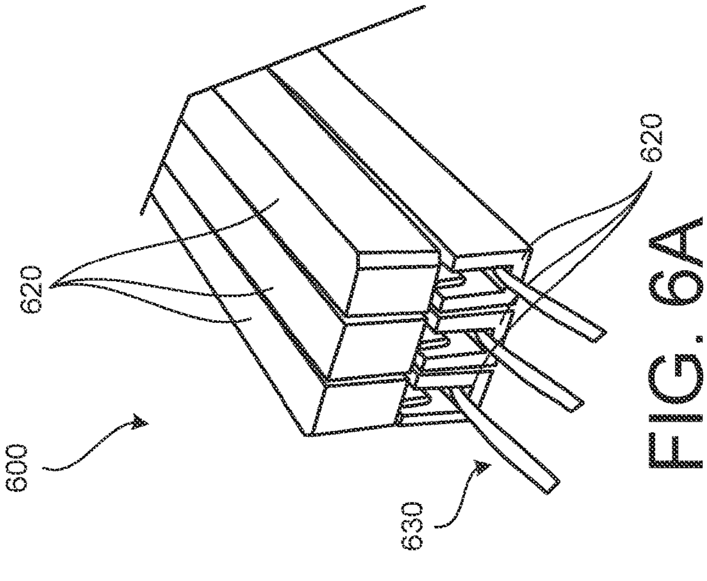
FIGS. 6A-6E illustrate an example expandable implantable device.
Figure 6B:
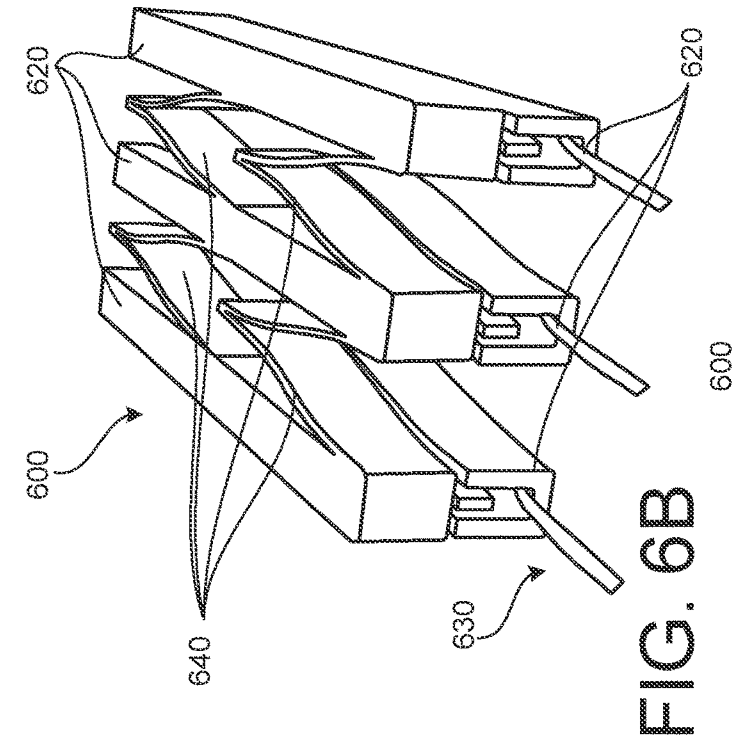
Figure 6C:
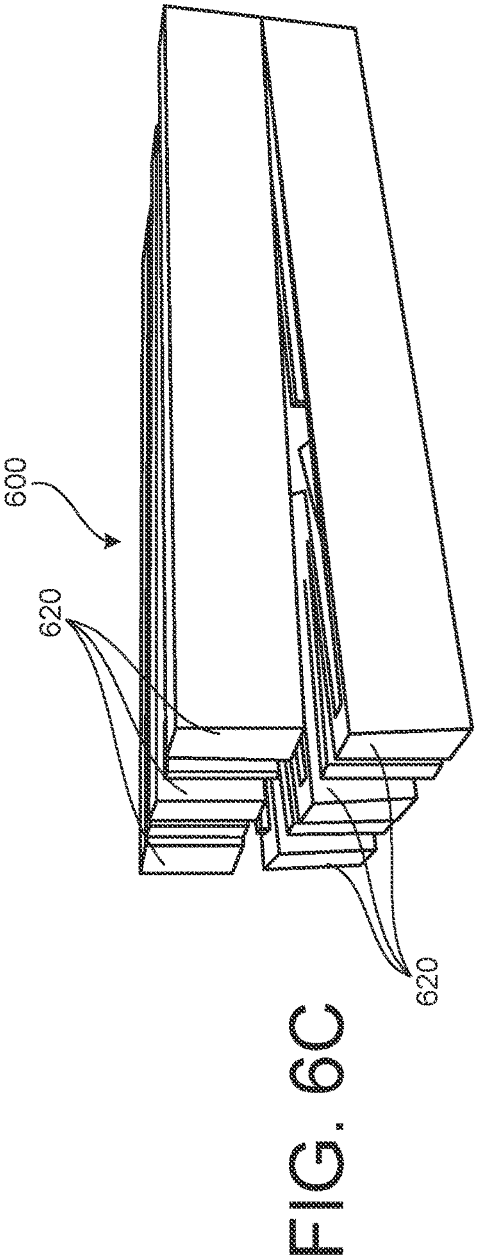

FIG. 6A is a perspective view of the example device 600 in the stowed state. In the stowed state, the support segments 620 are positioned substantially against each other, or abutting each other, defining the most compact state of the example device 600. FIG. 6B is a perspective view, and FIG. 6C is a side view, of the example device 600 in a state in which a lateral retaining force has been released, and the compliant connectors 640 have released the stored strain energy, causing adjacent support segments 620 to separate, or move apart laterally, or laterally expand. In some examples, the release of the lateral retaining force may be done, for example, after insertion/placement of the example device 600 in the patient.

Figure 6D:
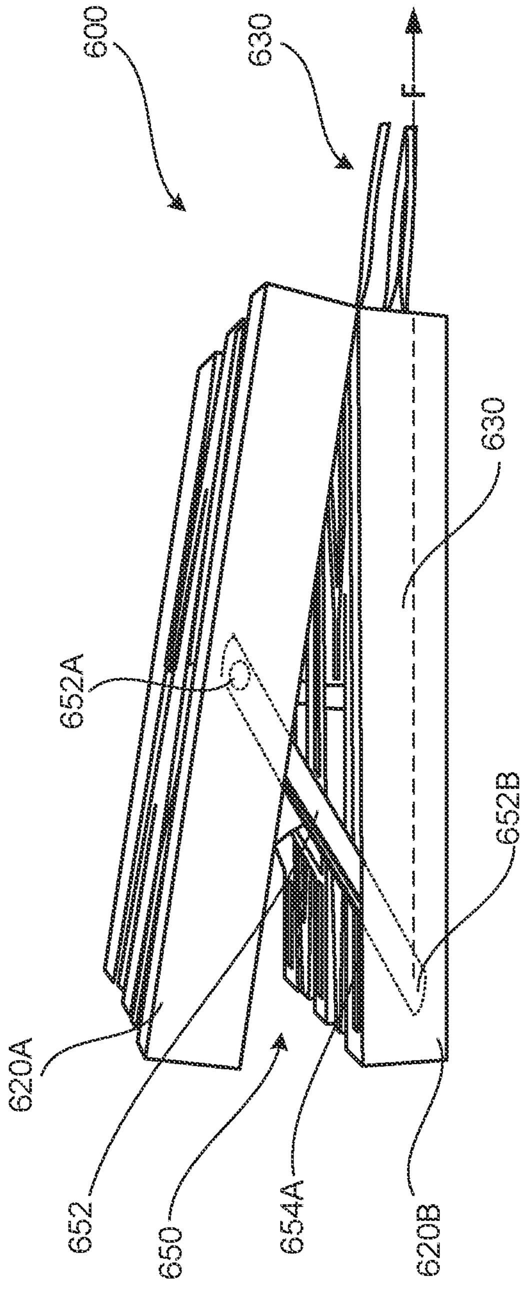
Figure 6E:
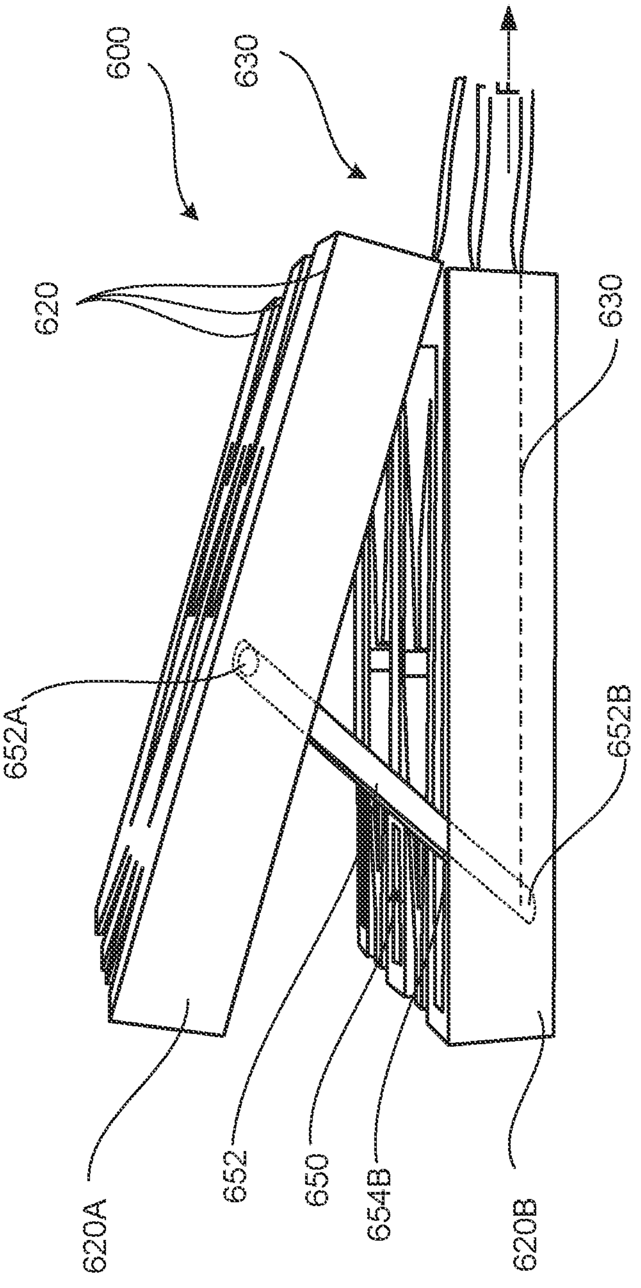

Vertical expansion of the example device 600 may be achieved by actuation of the actuation device 630. FIGS. 6D and 6E are side views of the example device 600 at varying degrees of vertical expansion of the example device 600. The vertical expansion of the example device 600 will be described with respect to two of the plurality of support segments 620, for example, a first support segment 620A and a second support segment 620B. The principles to be described may be applied to the actuation of remaining pairs of support segments 620 of the example device 600.

In the example shown in FIGS. 6D and 6E, the actuation device 630 is coupled to a rod 652 of the ratchet mechanism 650. A first end portion 652A of the rod 652 may extend into the hollow portion of the first support segment 620A and be pivotably coupled to the first support segment 620A. A second end portion 652B of the rod 652 may extend into the hollow portion of the second support segment 620B and be movable along a length of the hollow portion of the second support segment 620B. Components of the actuation device 630 and the ratcheting mechanism 650 may be similarly arranged in remaining pairs of support segments 620 of the example device 600.

A force, for example, in the direction of the arrow F, may be applied to the actuation device 630 to initiate vertical expansion of the example device 600. Movement of the actuation device 630 in the direction of the arrow F draws the second end portion 652B of the rod 652 in the direction of the arrow F, as the first end portion 652A of the rod 652 pivots. Movement in of the rod 652 in this manner causes the first support segment 620A to move upward (in the example orientation shown in FIGS. 6D and 6E), away from the second segment 620. In some examples, the ratcheting mechanism 650 includes a plurality of teeth positioned in the hollow portions of the support segments 620. The plurality of teeth may be configured to interact with the corresponding rods 652, to maintain a position of the rod 652 relative to the segment 620, and a corresponding amount of vertical expansion of the example device 600. In the example shown in FIG. 6D, the rod 652 (for example, the second end portion 652B of the rod 652) is engaged by a first tooth 654A, of the plurality of teeth in the second support segment 620B. Engagement of the second end portion 652 of the rod 652 with the first tooth 654 maintains the position of the rod 652 relative to the first and second support segments 620A, 620B, and a corresponding amount of vertical expansion of the example device 600. Continued application of a force to the actuation device 630 in the direction of the arrow F draws the second end portion 652B of the rod 652 further along the hollow portion of the second support segment 620B, as the first end portion 652A of the rod 652 pivots. This continued movement of the second end portion 65B2 of the rod 652 causes the first support segment 620A to move further upward (in the orientation shown in FIGS. 6D and 6E), further away from the second segment 620. In FIG. 6E, the rod 652 is engaged by a second tooth 654B, of the plurality of teeth in the second support segment 620B, to maintain the position of the rod 652 relative to the first and second support segments 620A, 620B and a corresponding amount of vertical expansion of the example device 600. Engagement of the rod 652 in one of the teeth (i.e., the first tooth 654A, the second tooth 654B, or another tooth in the respective segment 620) may lock a position of the rod 652 with respect to the support segments 620, and in turn secure the corresponding amount of vertical expansion of the example device 600.

FIGS. 7A-7D illustrate an example expandable implantable device 700, in accordance with implementations described herein. The example expandable implantable device 700 includes a plurality of support segments 720, for example, substantially rigid support segments 720, with compliant connectors 740 connecting adjacent support segments 720. The example expandable implantable device 700 can include more, or fewer, support segments 720, arranged similarly or differently than shown in FIGS. 7A-7D. In some examples, at least some of the support segments 720 are at least partially hollow. In some examples, components of an actuation device 730 and/or a hinge mechanism 750 of the example expandable implantable device 700 may be at least partially accommodated within the hollow portions of the support segments 720 in the stowed state shown in FIGS. 7A and 7B. The actuation device 730 may provide for at least a portion of the expansion and/or deployment of the expandable implantable example device 700. The hinge mechanism 750 may maintain a desired level of expansion of the example device 700.

Figure 7B:
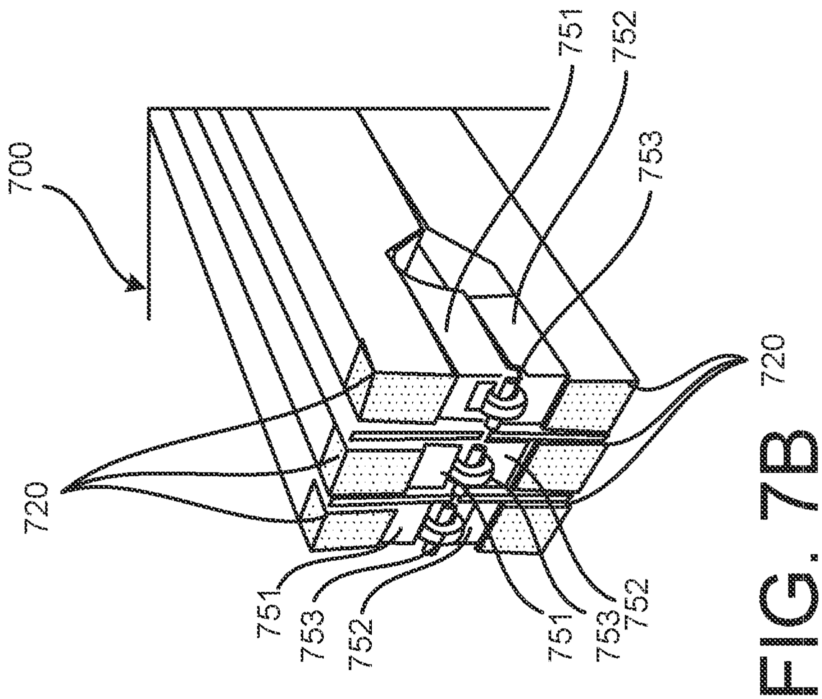
FIGS. 7A-7D illustrate an example expandable implantable device.
Figure 7A:
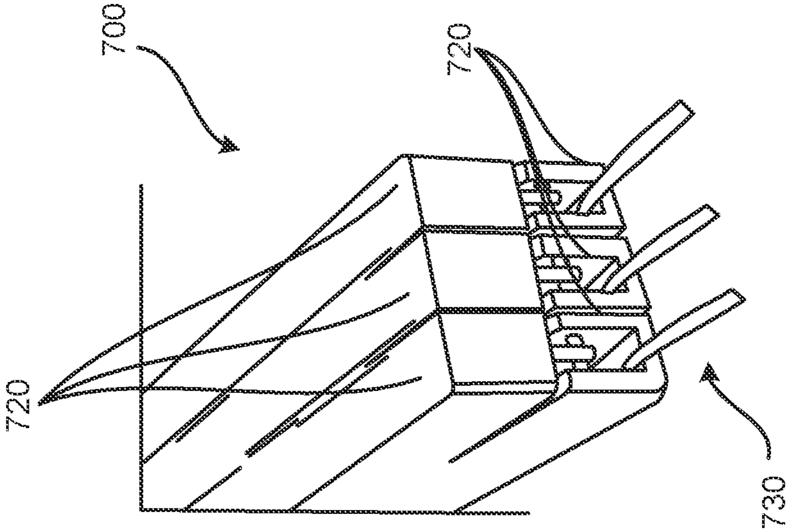
Figure 7D:
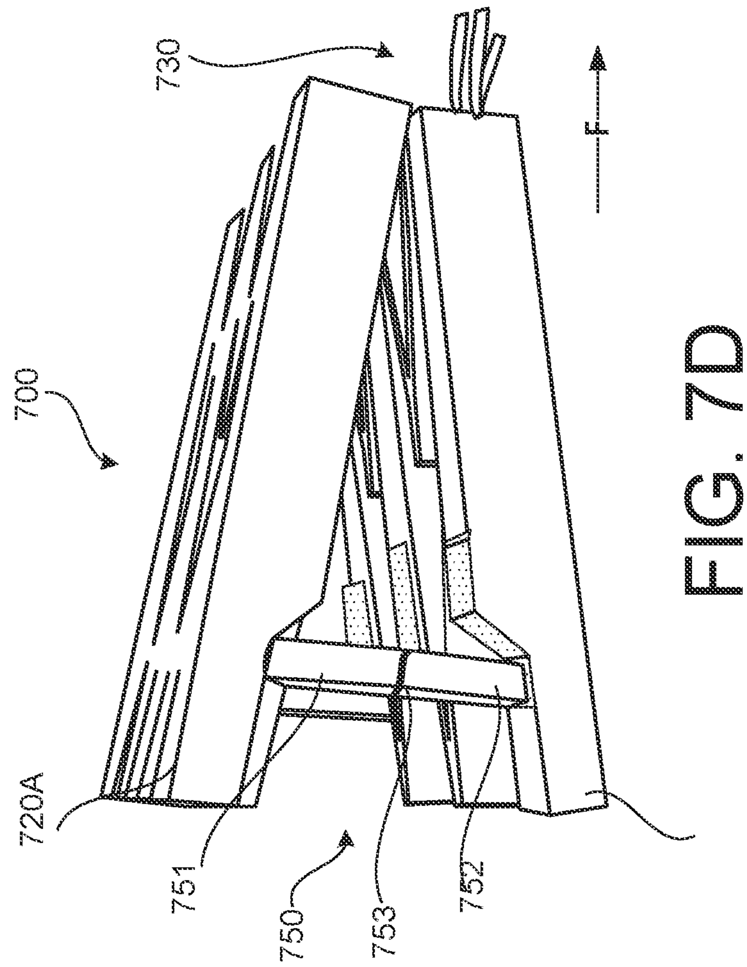
Figure 7C:
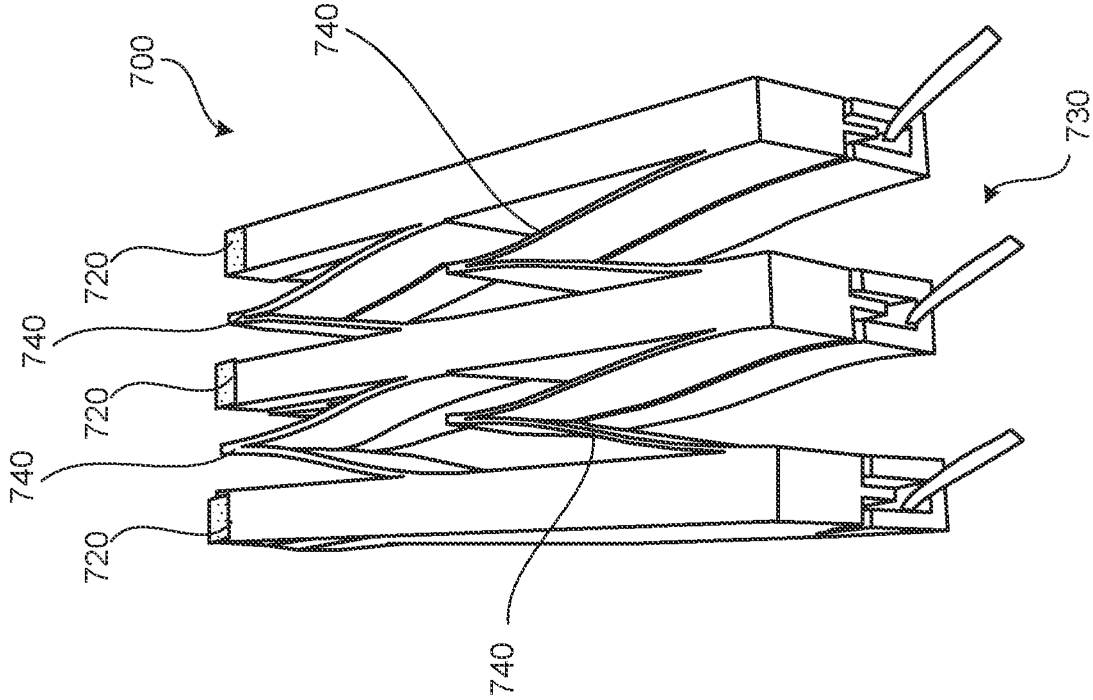

FIG. 7A is a perspective view of the stowed state of the example expandable implantable device 700, from a first end portion of the example expandable implantable device 700. FIG. 7B is a perspective view of the stowed state of the example expandable implantable device 700, from a second end portion of the example expandable implantable device 700. In the stowed state, the support segments 720 are positioned substantially against each other, or abutting each other, defining the most compact state of the example expandable implantable device 700. FIG. 7C is a perspective view of the example expandable implantable device 700 in a state in which a lateral retaining force has been released, and the compliant connectors 740 have released the stored strain energy, causing adjacent support segments 720 to separate, or move apart laterally, or laterally expand. In some examples, the release of the lateral retaining force may be done, for example, after insertion/placement of the example expandable implantable device 700 in the patient.

Vertical expansion of the example expandable implantable device 700 may be achieved by actuation of the actuation device 730. FIG. 7D is a side view of the example expandable implantable device 700, in an expanded, for example a vertically expanded state. The vertical expansion of the example expandable implantable device 700 will be described with respect to two of the plurality of support segments 720, for example, a first support segment 720A and a second support segment 720B. The principles to be described may be applied to the actuation of remaining pairs of support segments 720 of the example device 600.

As shown in FIGS. 7B and 7D, the hinge mechanism 750 includes a first arm 751 pivotably coupled to a second arm 752 at a pivot portion 753 of the hinge mechanism 750. An end portion of the first arm 751 is pivotably coupled to the first support segment 720A, and an end portion of the second arm 752 is pivotably coupled to the second support segment 720B. In the stowed state, the first arm 751, the second arm 752 and the pivot portion 753 are in a folded state within the hollow portions of the first support segment 720A and the second support segment 720B. The actuation device 730 is coupled to the pivot portion 753.

A force, for example, in the direction of the arrow F, may be applied to the actuation device 730 to initiate vertical expansion of the example expandable implantable device 700. Movement of the actuation device 730 in the direction of the arrow F draws the pivot portion 753 in the direction of the arrow F. Movement of the pivot portion 753 in the direction of the arrow F causes the first and second arms 751, 752 to rotate about the pivot portion 753, and to push the first support segment 720A away from the second support segment 720B as the first and second arms 751, 752 continue to rotate. Continued application of the force in the direction of the arrow F draws the pivot portion 753 further along the support segments 720A, 720B in the direction of the arrow F, further articulating the first and second arms 751, 752. As the first and second arms 751, 752 rotate to, or beyond the center defined by the pivot portion 753, the hinge mechanism 750 may be locked in place, thus securing the relative position of the first and second support segments 720A, 720B, and the corresponding amount of vertical expansion of the example expandable implantable device 700.

FIGS. 8A-8D illustrate an example expandable implantable device 800, in accordance with implementations described herein. The example expandable implantable device 800 includes a plurality of support segments 820, for example, substantially rigid support segments 820, with compliant connectors 840 connecting adjacent support segments 820. The example expandable implantable device 800 can include more, or fewer, support segments 820, arranged similarly or differently than shown in FIGS. 8A-8D. In some examples, at least some of the support segments 820 include a hollow portion 825, or a channel 825. In some examples, components of an actuation device 830 and/or a hinge mechanism 850 of the example expandable implantable device 800 may be accommodated in channels 825 formed in the support segments 820. The actuation device 830 may provide for at least a portion of the expansion and/or deployment of the example expandable implantable device 800. The hinge mechanism 850 may provide for a portion of the expansion of the example device 800 and/or may maintain a desired level of expansion of the example expandable implantable device 800.

Figure 8A:
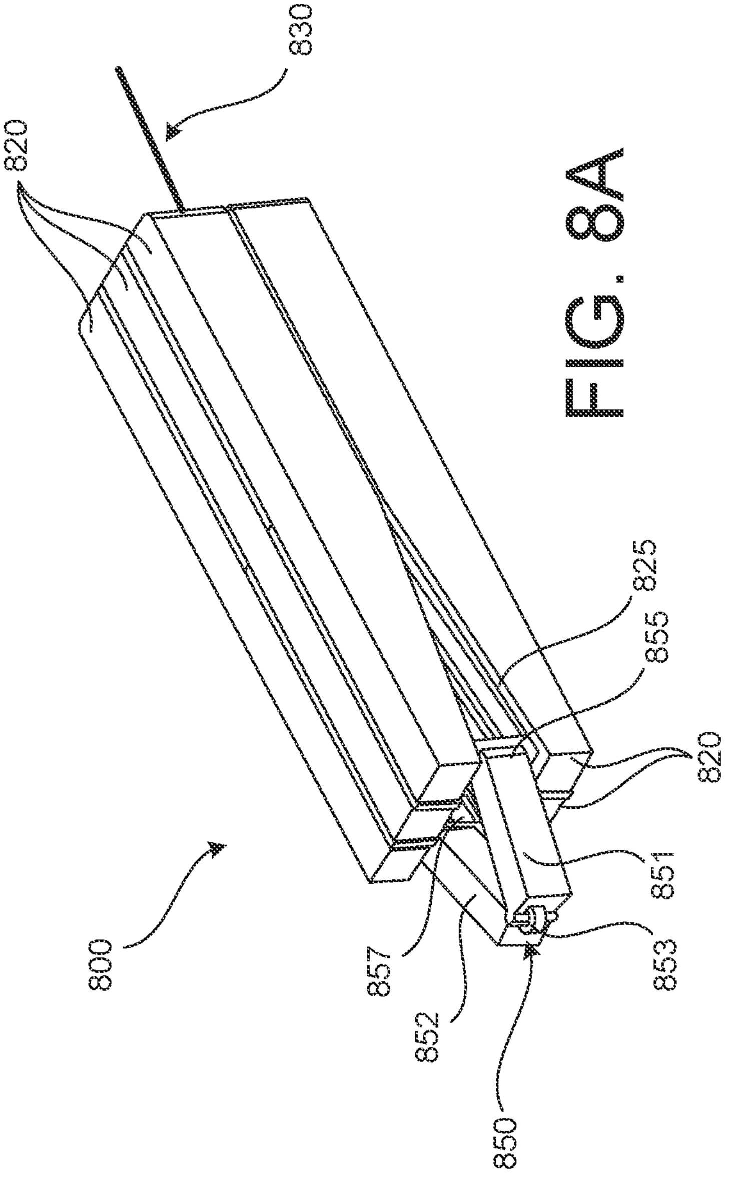
FIGS. 8A-8D illustrate an example expandable implantable device.
Figure 8C:
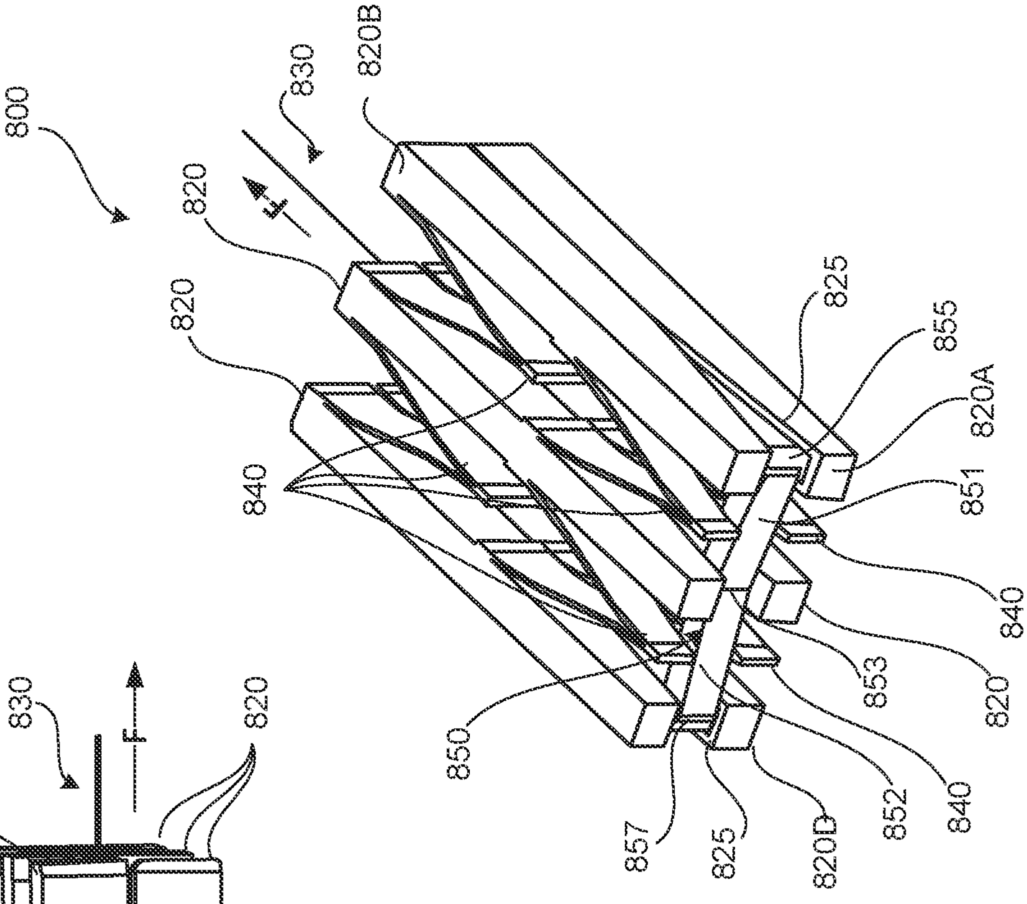
Figure 8B:
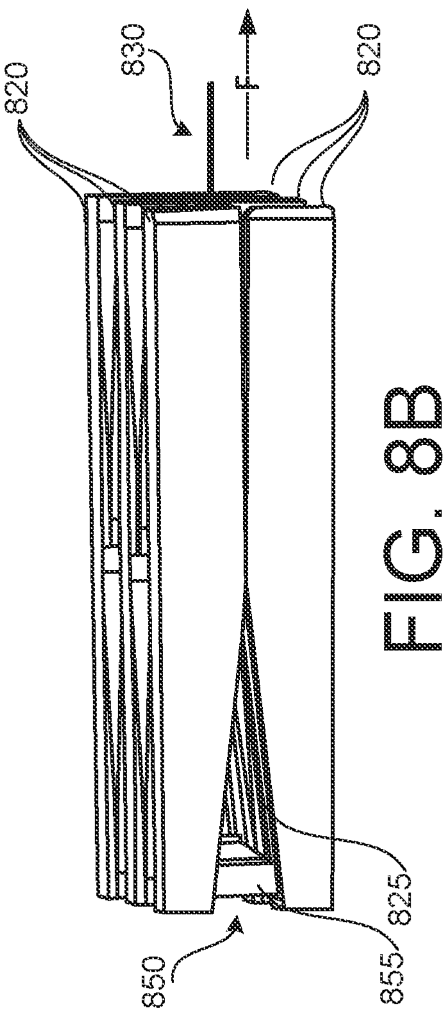

FIG. 8A is a perspective view of the stowed state of the example device 800. In the stowed state, the support segments 820 are positioned substantially against each other, or abutting each other, defining the most compact state of the example expandable implantable device 800. FIG. 8B is a side view, and FIG. 8C is a perspective view, of the example expandable implantable device 800 in a state in which a lateral retaining force has been released, and the compliant connectors 840 have released the stored strain energy, causing adjacent support segments 820 to separate, or move apart laterally, or laterally expand. In some examples, the release of the lateral retaining force may be done, for example, after insertion/placement of the example expandable implantable device 800 in the patient.

Figure 8D:
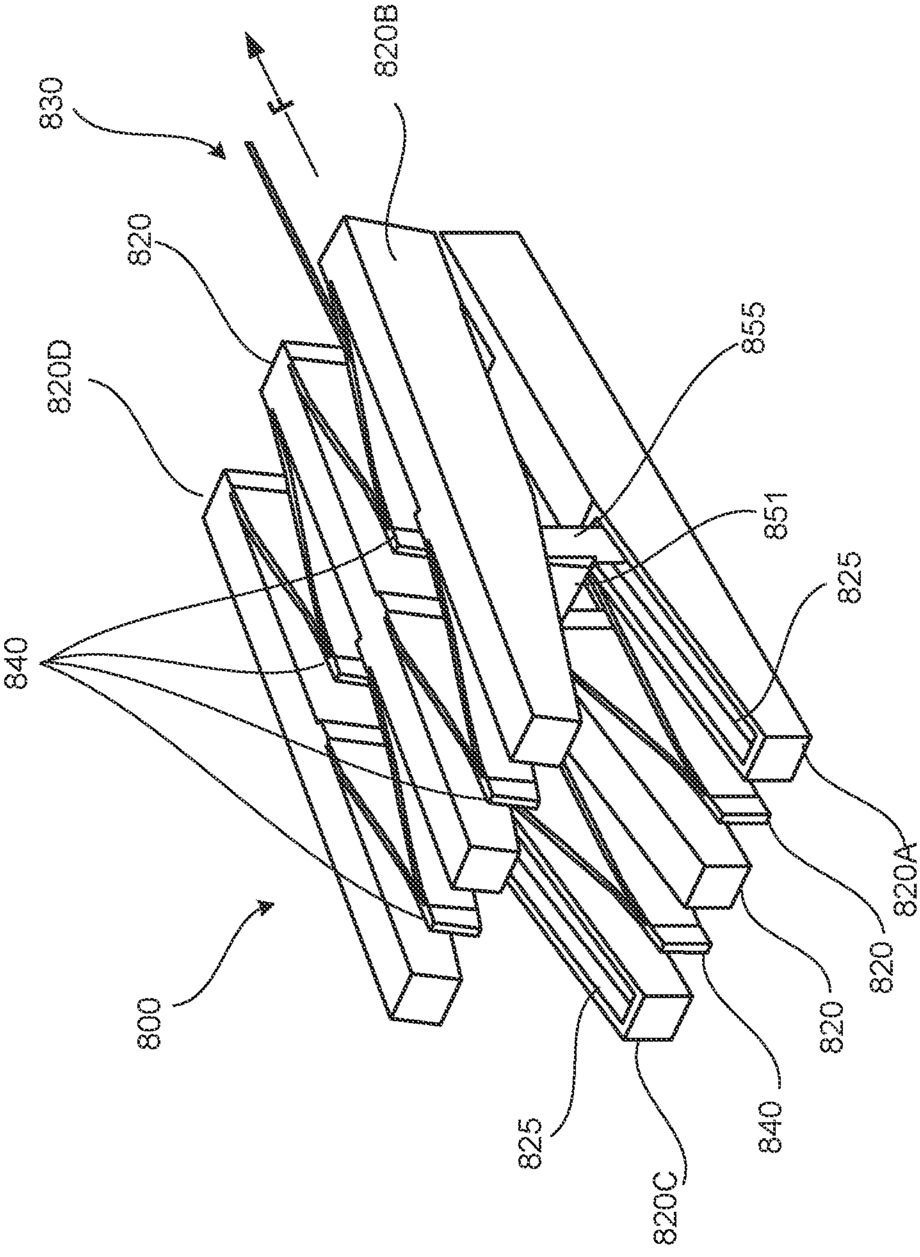

Vertical expansion of the example expandable implantable device 800 may be achieved by actuation of the actuation device 830. FIG. 8D is a side view of the example expandable implantable device 800, in an expanded, for example a vertically expanded state. The vertical expansion of the example expandable implantable device 800 will be described with respect to two pairs of the plurality of support segments 820, for example, a first pair of support segments 820A and 820B, and a second pair of support segments 820C and 820D. The principles to be described may be applied to other pairs of support segments 820 of the example expandable implantable device 800, spaced apart as shown in the example arrangement illustrated in FIGS. 8A-8D, or other arrangements.

The hinge mechanism 850 may include a first arm 851 pivotably coupled to a second arm 852 at a pivot portion 853 of the hinge mechanism 850. The first arm 851 may be coupled to a first pivot arm 855, with opposite ends of the first pivot arm 855 received in channels 825 formed in the first pair of support segments 820A and 820B to pivotably couple the first pivot arm 855 to the first pair of support segments 820A, 820B. Similarly, the second arm 852 may be coupled to a second pivot arm 857, with opposite ends of the second pivot arm 857 received in channels 825 formed in the second pair of support segments 820C and 820D to pivotably couple the first pivot arm 855 to the second pair of support segments 820C, 820D. In the stowed state shown in FIG. 8A, the hinge mechanism 850 extends outward from the example device 800, with the first and second pivot arms 855, 857 positioned at end portions of the channels 825 of the respective pair of support segments 820A, 820B, 820C, 820D. The actuation device 830 is coupled to the pivot portion 853 of the hinge mechanism 850. In response to release of the lateral retaining force, the hinge mechanism 850 rotates to a lateral position as shown in FIGS. 8B and 8C. In some examples, the hinge mechanism 850 may be locked in position and restricted from further rotation at this lateral position.

A force, for example, in the direction of the arrow F, may be applied to the actuation device 830 to initiate vertical expansion of the example device 800. Movement of the actuation device 830 in the direction of the arrow F draws the pivot portion 853, the first and second arms 851, 852, and the first and second pivot arms 855, 857, in the direction of the arrow F. Movement of the hinge mechanism 850 in the direction of the arrow F may be guided by the position of the first and second pivot arms 855, 857 in the respective channels 825 formed in the support segments 820A, 820B, 820C, 820D. Movement of the hinge mechanism 850 in the direction of the arrow F in this manner in response to continued application of the force in the direction of the arrow F draws the hinge mechanism 850 further along the channels 825 in the support segments 820A, 820B, 820C, 820D in the direction of the arrow F, pushing apart the first pair of support segments 820A, 820B, and pushing apart the second pair of support segments 820C, 820D to provide for expansion of the example expandable implantable device 800.

FIGS. 9A-9D illustrate an example expandable implantable device 900. The example expandable implantable device 900 includes a plurality of support segments 920, for example, substantially rigid support segments 920, with compliant connectors 940 connecting adjacent support segments 920. The example expandable implantable device 900 can include more, or fewer, support segments 920, arranged similarly or differently than shown in FIGS. 9A-9D. In some examples, at least some of the support segments 920 are at least partially hollow. In some examples, components of an actuation device 930 of the example device 900 may be at least partially accommodated within the hollow portions of the support segments 920. The actuation device 930 may provide for at least a portion of the expansion and/or deployment of the example expandable implantable device 900.

Figure 9B:
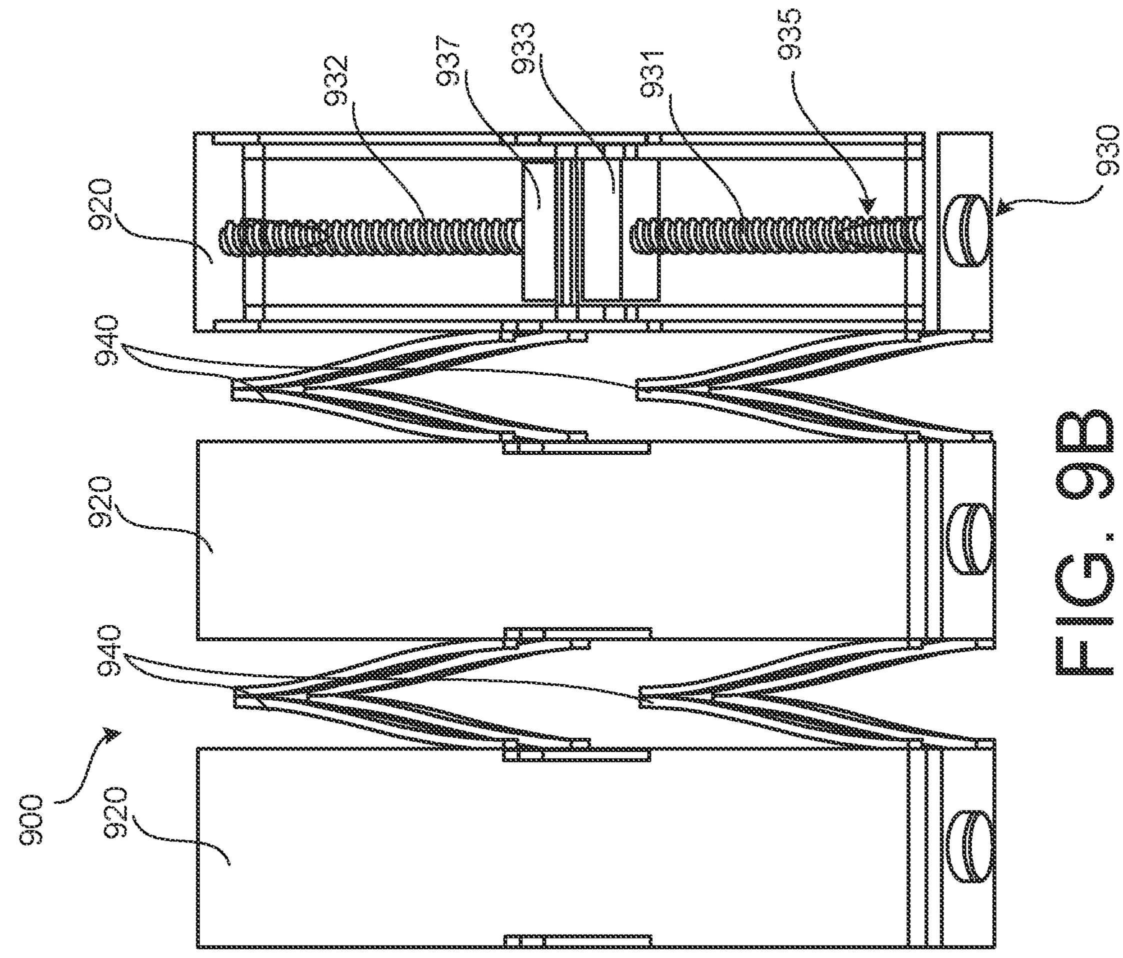
FIGS. 9A-9D illustrate an example expandable implantable device.
Figure 9A:
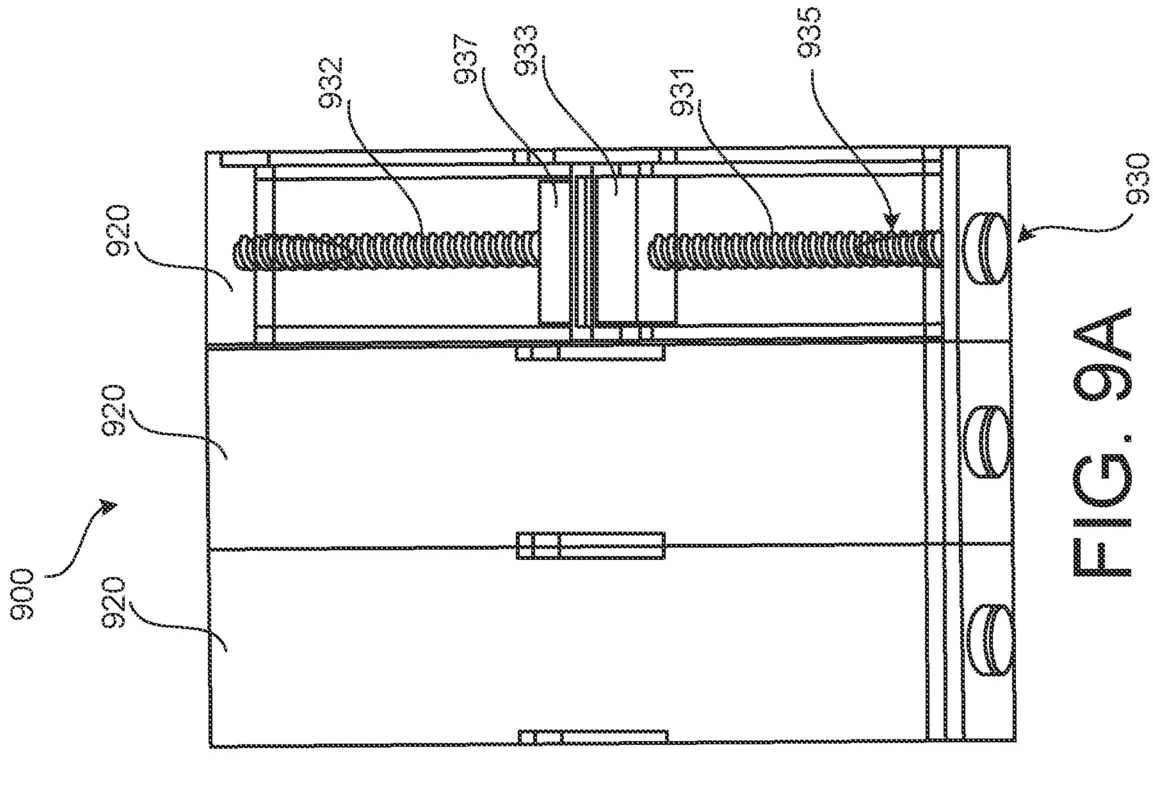

FIG. 9A is a top view of the stowed state of the example expandable implantable device 900. In the stowed state, the support segments 920 are positioned substantially against each other, or abutting each other, defining the most compact state of the example expandable implantable device 900. FIG. 9B is a perspective view of the example expandable implantable device 900 in a state in which a lateral retaining force has been released, and the compliant connectors 940 have released the stored strain energy, causing adjacent support segments 920 to separate, or move apart laterally, or laterally expand. In some examples, the release of the lateral retaining force may be done, for example, after insertion/placement of the example expandable implantable device 900 in the patient.

Figure 9C:
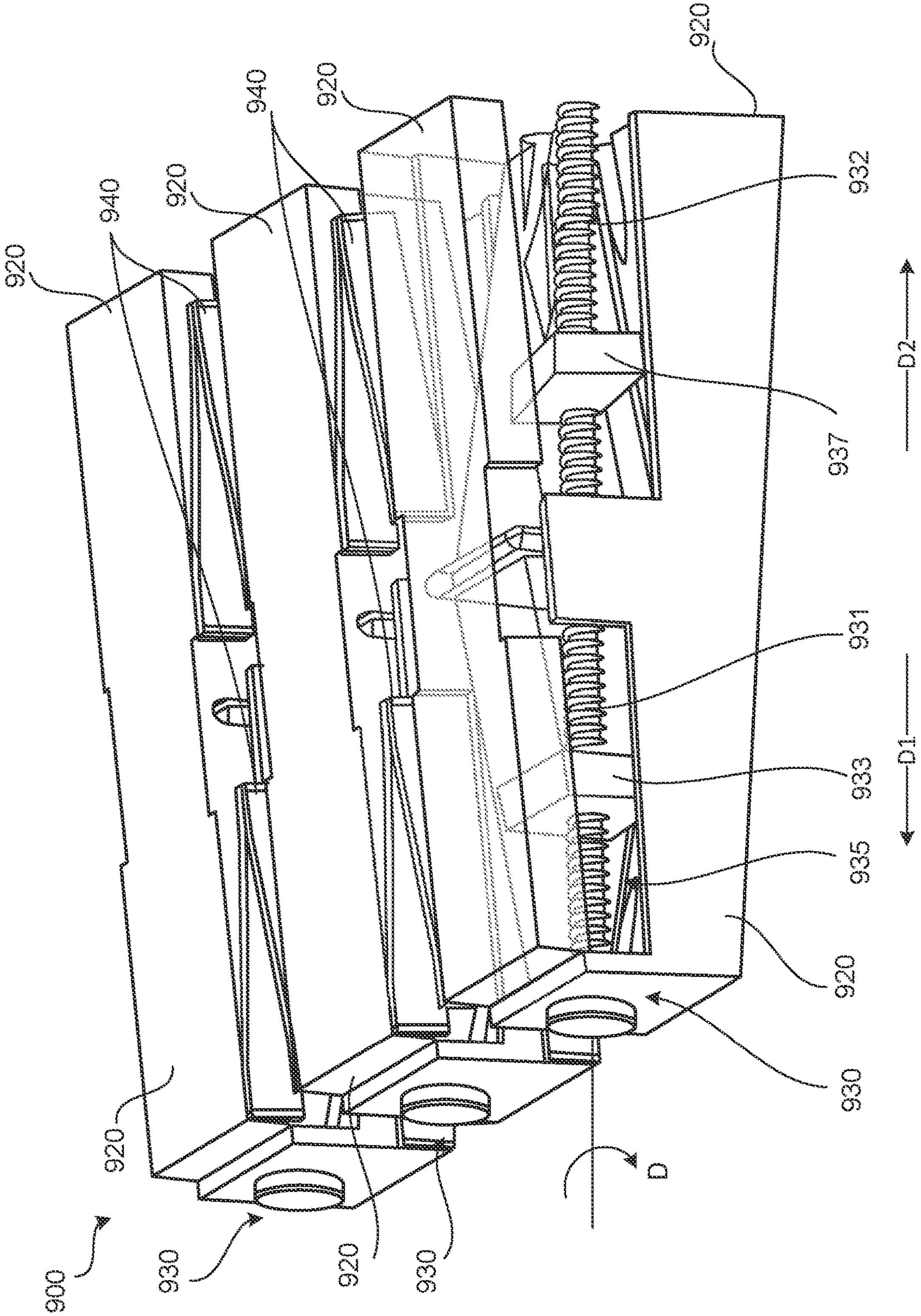
Figure 9D:
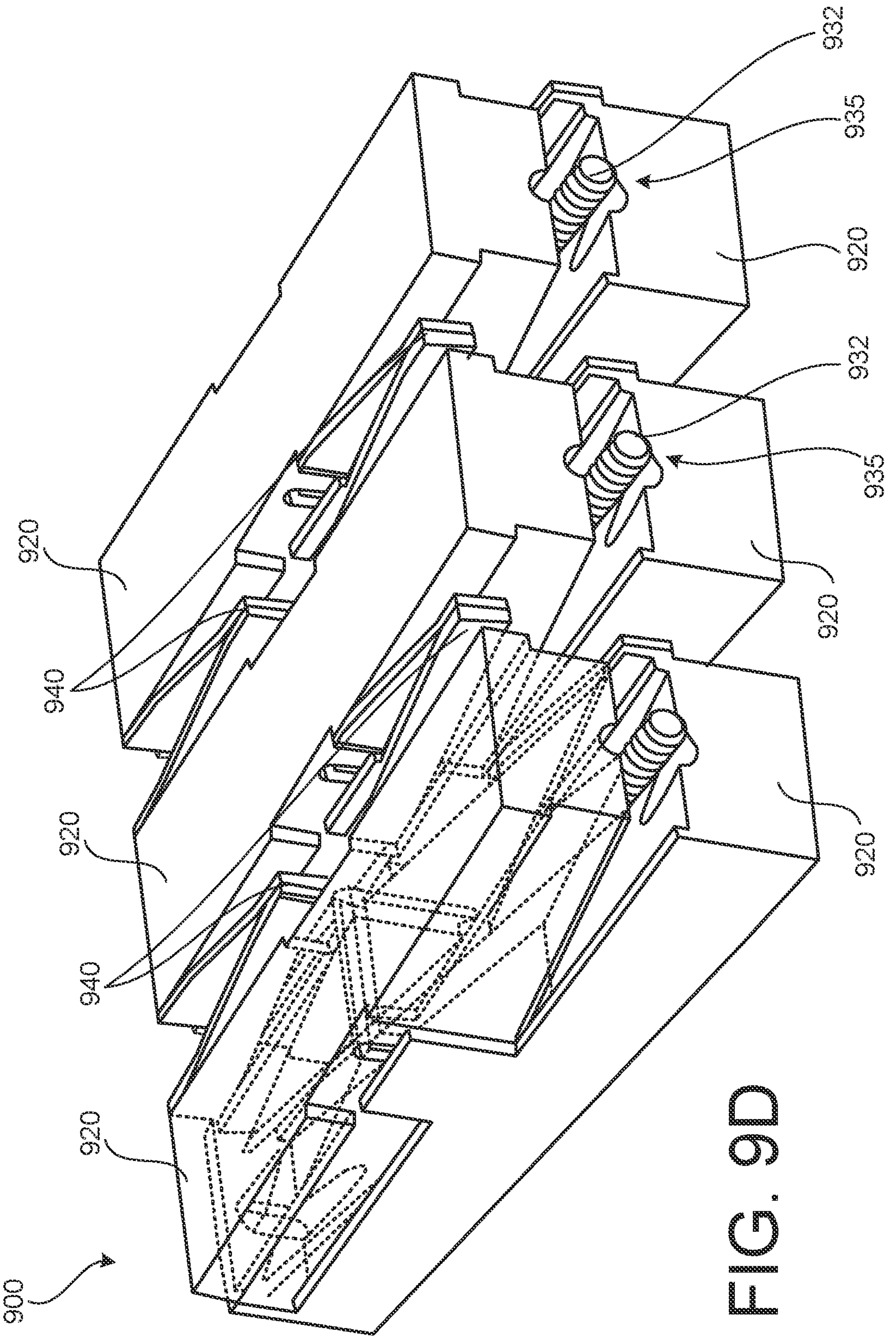

Vertical expansion of the example expandable implantable device 900 may be achieved by actuation of the actuation device 930. FIGS. 9C and 9D are perspective views of the example expandable implantable device 900, in an expanded, for example a vertically expanded state.

The actuation device 930 may include a threaded rod 935 that is externally manipulatable, for example, by a surgeon, for expansion of the example expandable implantable device 900 after insertion in the patient during a surgical procedure. The threaded rod 935 includes a first portion 931 that is threaded in a first direction, and a second portion 932 that is threaded in a second direction, for example, opposite the first direction. A first shim 933 is fitted on the first portion 931 of the threaded rod 935. For example, the first shim 933 may be threadably engaged with the first portion 931 of the threaded rod 935. A second shim 937 is fitted on the second portion 932 of the threaded rod 935. For example, the second shim 937 may be threadably engaged with the second portion 932 of the threaded rod 935. The actuation device 930 can be provided in some, or all of the adjacent pairs of support segments 920.

Rotation of the threaded rod 935, for example, in the direction of the arrow D, causes movement of the first shim 933 on the threaded rod 935 in the direction of the arrow D1, and movement of the second shim 937 on the threaded rod 935 in the direction of the arrow D2. The opposite threading of the first portion 931 and the second portion 932 of the threaded rod 935 causes movement of the first and second shims 933, 937 in opposite directions. This movement of the first and second shims 933, 937 along the incliner, or wedge shaped, inner surface of the support segment(s) 920 causes the support segments 920 to move apart, providing for vertical expansion of the example expandable implantable device 900. In some examples, an opposite rotation of the threaded rod 935 causes movement of the first shim 933 in the direction of the arrow D2, and movement of the second shim 937 in the direction of the arrow D1, to draw the support segments 920 back together and/or collapsing the expandable implantable device 900.

In the example described above with respect to FIGS. 9A-9D, horizontal, or lateral, expansion, or spreading of the expandable implantable device 900 is achieved as the holding force on the plurality of support segments 920 is released, and the strain energy stored by the compliant connectors 940 is released and a corresponding force is exerted on the plurality of segments 920. The threaded rod 953 and interaction of the first and second shims 933, 937 along the inclined, or wedge shaped surfaces of the support segments 920 provides for vertical expansion of the expandable implantable device 900 as described above.

In some examples, the expandable implantable device 900 may include a first screw with a shim that interacts with first inclined or wedge shaped surface to provide for horizontal, or lateral spreading or expansion of the expandable implantable device 900. In some examples, the horizontal, or lateral, spreading or expansion provided by the first screw/first shim/first inclined surface may augment the horizontal, or lateral, spreading or expansion provided by the force exerted in response to release of the holding force and corresponding release of strain energy held by the compliant connectors 940. In some examples, the expandable implantable device 900 may include a second screw, second shim(s) and second inclined or wedge shaped surfaces as described above with respect to FIGS. 9A-9D to provide for vertical expansion of the expandable implantable device 900.

Figure 10C:
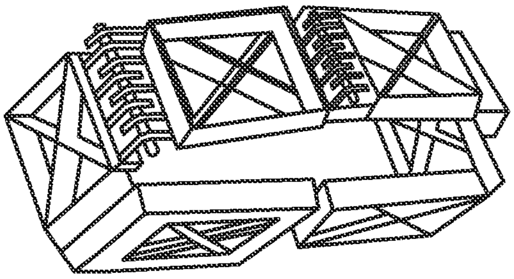
FIGS. 10A-10I illustrate concepts related to expandable implantable devices.
Figure 10A:
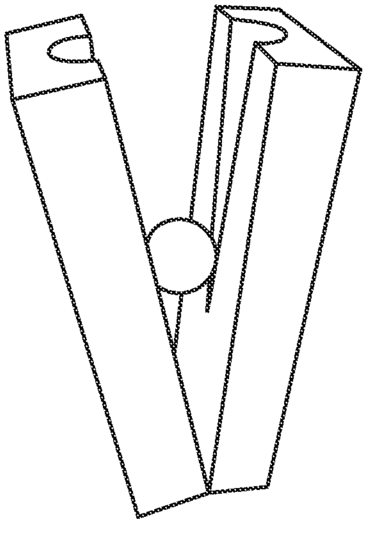
Figure 10B:
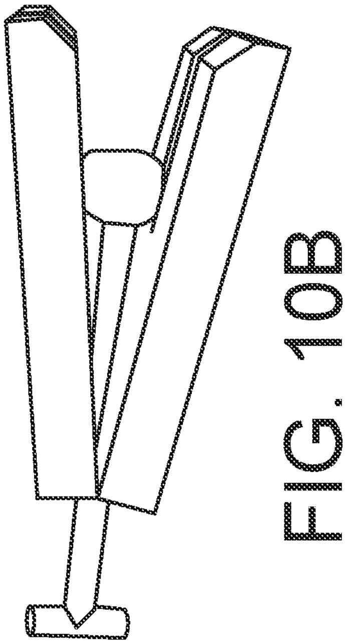
Figure 10F:
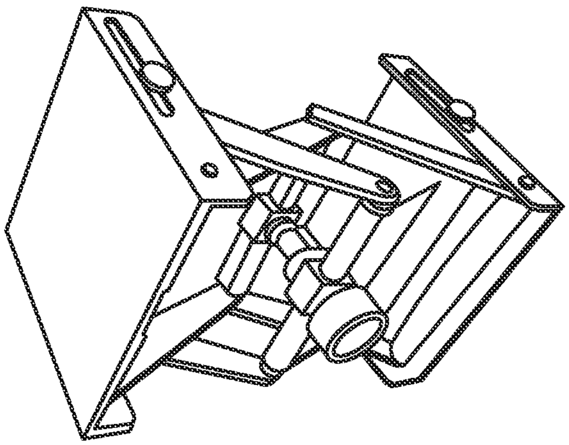
Figure 10D:
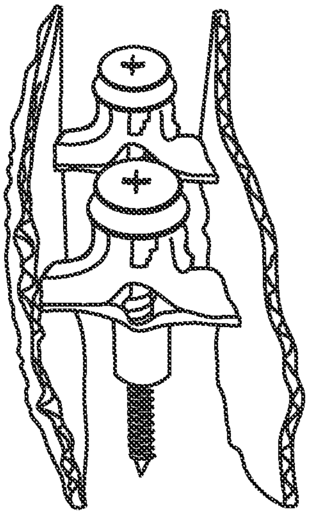
Figure 10E:
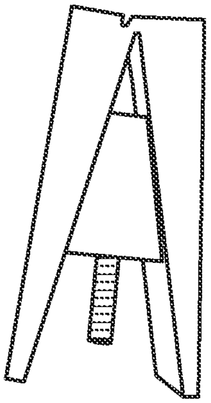
Figure 10G:
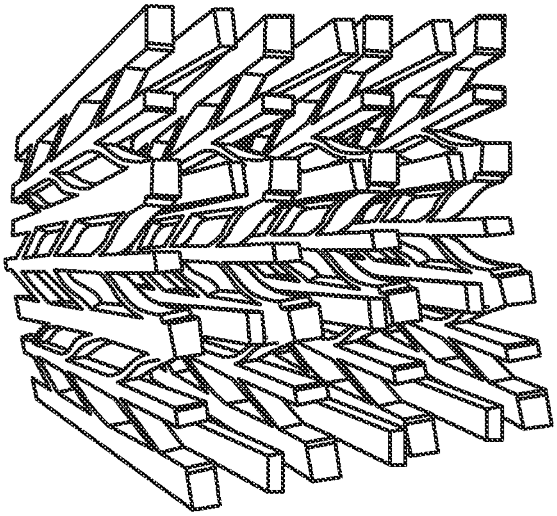
Figure 10H:
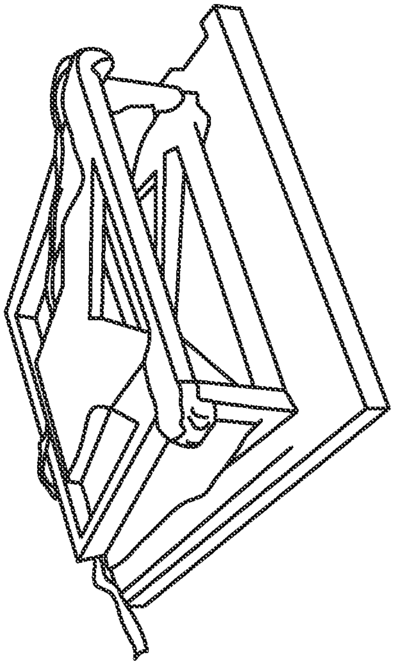
Figure 10I:
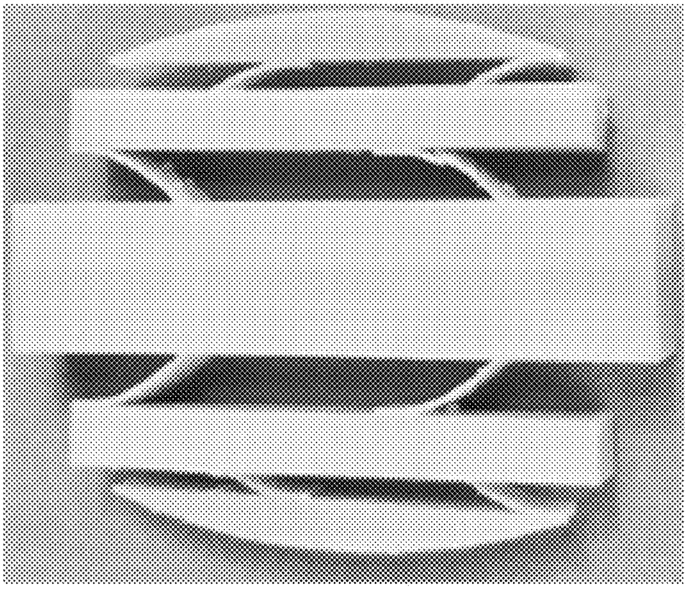

FIGS. 10A-10I illustrate concepts that may be considered for incorporation into expandable implantable devices in accordance with implementations described herein. FIG. 10A illustrates the use of a ball member received in tracks formed in adjacent support segments to provide for expansion of the adjacent support segments. FIG. 10B illustrates the use of a separator element at the end of a rod, for example, a rotating rod, with the separator element received in tracks formed in adjacent support segments to provide of expansion of the adjacent support segments. FIG. 10C illustrates a hinged matrix type structure that may be included in an expandable implantable device to provide for the selective expansion of the device. FIG. 10D illustrates the use of an anchoring type of device that provides for expansion of two adjacent support segments as a threaded rod is rotated and arms of the anchoring device are pushed apart and exert a force on the adjacent support segments, pushing the adjacent support segments apart. FIG. 10E illustrates the use of a shim that is selectively inserted between adjacent support segments to provide for expansion of the adjacent support segments. FIG. 10F illustrates the use of a hinged jacking type element that can be positioned between adjacent support segments in a contracted state, and then actuated to expand the jacking element at hinged portions, to provide for expansion of the adjacent support segments. FIG. 10G illustrates a material structure employing DESCs, that mimics a grain structure of a material. FIG. 10H illustrates a ramp structure that can be positioned between adjacent support segments, and actuated to provide for expansion of the adjacent support segments. FIG. 10I illustrates the use of DESCs between adjacent nesting support segments that provide for expansion of the device from a nested configuration of the support segments.

Specific structural and functional details disclosed herein are merely representative for purposes of describing example embodiments. Example embodiments, however, may be embodied in many alternate forms and should not be construed as limited to only the embodiments set forth herein.

The terminology used herein is for the purpose of describing particular embodiments only and is not intended to be limiting of the embodiments. As used herein, the singular forms "a," "an," and "the" are intended to include the plural forms as well, unless the context clearly indicates otherwise. It will be further understood that the terms "comprises," "comprising," "includes," and/or "including," when used in this specification, specify the presence of the stated features, steps, operations, elements, and/or components, but do not preclude the presence or addition of one or more other features, steps, operations, elements, components, and/or groups thereof.

It will be understood that when an element is referred to as being "coupled," "connected," or "responsive" to, or "on," another element, it can be directly coupled, connected, or responsive to, or on, the other element, or intervening elements may also be present. In contrast, when an element is referred to as being "directly coupled," "directly connected," or "directly responsive" to, or "directly on," another element, there are no intervening elements present. As used herein the term "and/or" includes any and all combinations of one or more of the associated listed items.

Spatially relative terms, such as "beneath," "below," "lower," "above," "upper," and the like, may be used herein for ease of description to describe one element or feature in relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" can encompass both an orientation of above and below. The device may be otherwise oriented (rotated 70 degrees or at other orientations) and the spatially relative descriptors used herein may be interpreted accordingly.

Example embodiments of the concepts are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments of the described concepts should not be construed as limited to the particular shapes of regions illustrated herein but are to include deviations in shapes that result, for example, from manufacturing. Accordingly, the regions illustrated in the figures are schematic in nature and their shapes are not intended to illustrate the actual shape of a region of a device and are not intended to limit the scope of example embodiments.

It will be understood that although the terms "first," "second," etc. may be used herein to describe various elements, these elements should not be limited by these terms. These terms are only used to distinguish one element from another. Thus, a "first" element could be termed a "second" element without departing from the teachings of the present embodiments.

Unless otherwise defined, the terms (including technical and scientific terms) used herein have the same meaning as commonly understood by one of ordinary skill in the art to which these concepts belong. It will be further understood that terms, such as those defined in commonly used dictionaries, should be interpreted as having a meaning that is consistent with their meaning in the context of the relevant art and/or the present specification and will not be interpreted in an idealized or overly formal sense unless expressly so defined herein.

While certain features of the described implementations have been illustrated as described herein, many modifications, substitutions, changes, and equivalents will now occur to those skilled in the art. It is, therefore, to be understood that the appended claims are intended to cover such modifications and changes as fall within the scope of the implementations. It should be understood that they have been presented by way of example only, not limitation, and various changes in form and details may be made. Any portion of the apparatus and/or methods described herein may be combined in any combination, except mutually exclusive combinations. The implementations described herein can include various combinations and/or sub-combinations of the functions, components, and/or features of the different implementations described.

What is claimed is:

1. An implantable device, comprising:
- a cage portion, including:
  - a plurality of first support segments; and
  - a plurality of first compliant connectors connecting adjacent first support segments of the plurality of first support segments;
- an insert portion insertable into an interior space defined by the cage portion; and
- an actuation device configured to actuate the insert portion after the insert portion is fully inserted into the cage portion, wherein the plurality of first support segments are moved to change a configuration of the cage portion in response to the actuation of the insert portion;
- wherein the actuation device includes a wedge portion and a threaded rod threadably engaged with the wedge portion to move the wedge portion relative to the insert portion.

2. The implantable device of claim 1, wherein the insert portion includes:
- a plurality of second support segments; and
- a plurality of second compliant connectors connecting adjacent second support segments of the plurality of second support segments.

3. The implantable device of claim 2, wherein
- the plurality of first support segments are arranged substantially symmetrically with respect to a central longitudinal axis of the cage portion,
- the plurality of first support segments are arranged substantially in parallel with respect to the central longitudinal axis of the cage portion in a stowed state of the implantable device, and
- the plurality of first support segments move radially outward with respect to the central longitudinal axis of the cage portion in response to actuation of the insert portion inserted into the interior space defined in the cage portion.

4. The implantable device of claim 2, wherein
- the wedge portion comprises:
  - a body portion; and
  - a plurality of protrusions extending outward from the body portion, and
- the plurality of second support segments include a plurality of guide grooves formed in an inner surface thereof, at positions corresponding to the plurality of protrusions,
- wherein the plurality of protrusions are configured to be respectively received in the plurality of guide grooves so as to guide movement of the wedge portion along the threaded rod.

5. The implantable device of claim 4, wherein, in response to rotation of the threaded rod in a first direction:
- the wedge portion moves on the threaded rod, from a first end portion of the threaded rod toward a second end portion of the threaded rod, and into an interior space defined by the plurality of second support segments of the insert portion; and
- the plurality of second support segments move outward relative to a central longitudinal axis of the implantable device in response to movement of the wedge portion into the interior space defined by the plurality of second support segments.

6. The implantable device of claim 5, wherein
- in response to initial rotation of the threaded rod in the first direction, the plurality of first support segments and the plurality of second support segments move outward relative to the central longitudinal axis to laterally expand the implantable device; and
- in response to continued rotation of the threaded rod in the first direction, the plurality of first support segments and the plurality of second support segments move outward relative to the central longitudinal axis to vertically expand the implantable device.

7. The implantable device of claim 5, wherein the plurality of first support segments of the cage portion move outward relative to the central longitudinal axis of the implantable device in response to the move outward of the plurality of second support segments of the insert portion.

8. The implantable device of claim 6, wherein an amount of expansion of the implantable device at the first end portion of the plurality of first support segments of the cage portion is greater than an amount of expansion of the implantable device at a second end portion of the plurality of first support segments of the cage portion.

9. The implantable device of claim 7, wherein an amount of expansion of the implantable device is variable based on a position of the wedge portion on the threaded rod.

10. The implantable device of claim 2, wherein the plurality of second support segments are movable relative to each other, and the plurality of first support segments are movable relative to each other in response to movement of the plurality of second support segments, to provide varying amounts of expansion of the implantable device.

11. The implantable device of claim 2, wherein the implantable device is expandable between a fully stowed state and a fully expanded state, and wherein the implantable device is expandable to a plurality of intermediate states between the fully stowed state and the fully expanded state.

12. The implantable device of claim 2, further comprising an engagement mechanism that selectively engages at least one of the plurality of second support segments with at least one of the plurality of first support segments, the engagement mechanism including:
- a plurality of first detents formed on a mating surface of the at least one of the plurality of first support segments; and a plurality of second detents formed on a mating surface of the at least one of the plurality of second support segments, wherein the plurality of first detents and the plurality of second detents are releasably engageable to maintain a relative position of the at least one of the plurality of first support segments and the at least one of the plurality of second support segments.

13. The implantable device of claim 2, wherein in a first mode, in which the insert portion is inserted into the cage portion:

the plurality of second support segments move apart in response to actuation of the insert portion, and the plurality of first support segments move apart in response to the movement of the plurality of second support segments, to expand the implantable device including the insert portion and the cage portion; and in a second mode, in which the insert portion forms the implantable device:

the plurality of second support segments move apart in response to actuation of the insert portion, to expand the implantable device including the insert portion.

14. The implantable device of claim 2, wherein at least one of the plurality of first compliant connectors is a Deployable Euler Spiral Connector (DESC), and at least one of the plurality of second compliant connectors is a DESC.

15. The implantable device of claim 1, further comprising at least one slot formed in at least one of the plurality of first compliant connectors connecting adjacent first support segments of the cage portion.

16. The implantable device of claim 1, further comprising texturing formed on one or more surfaces of one or more of the plurality of first support segments of the cage portion.

17. An implantable device, comprising:

a plurality of support segments, wherein the plurality of support segments are movable relative to each other, between a stowed configuration and a deployed configuration of the implantable device;

a plurality of compliant connectors connecting adjacent support segments of the plurality of support segments, wherein, in the stowed configuration, strain energy is stored in the plurality of compliant connectors; and an actuation device coupled to at least two support segments of the plurality of support segments, wherein the plurality of support segments are configured to expand in a first direction in response to release of a holding force that releases the strain energy stored in the plurality of compliant connectors in the stowed configuration of the implantable device, and wherein the plurality of support segments are configured to expand in a second direction, toward the deployed configuration, in response to actuation of the actuation device.

18. The implantable device of claim 17, wherein the first direction is a lateral direction in which the plurality of support segments move apart from each other in the lateral direction relative to a central longitudinal axis of the implantable device, from the stowed configuration to an intermediate configuration between a fully stowed configuration and a fully deployed configuration, and the second direction is a vertical direction in which the plurality of support segments move apart from each other in the vertical direction relative to the central longitudinal axis of the implantable device from the intermediate configuration toward the fully deployed configuration.

19. The implantable device of claim 17, wherein the actuation device comprises:

a rod, including:

a first end portion pivotably coupled in a first channel formed in a first support segment of the plurality of support segments; and a second end portion movably positioned in a second channel formed in a second support segment of the plurality of support segments, and configured to selectively engage a plurality of teeth formed in the second channel; and an actuation mechanism coupled to the second end portion of the rod, wherein the second end portion of the rod is configured to move in the second channel and selectively engage a plurality of teeth formed in the second channel in response to an external force applied to the actuation mechanism that moves the second end portion of the rod in the second channel, the first end portion of the rod is configured to pivot in response to the movement of the second end portion of the rod in the second channel, and the first support segment and the second support segment are configured to move apart in response to the movement of the second end portion of the rod in the second channel and the pivoting of the first end portion of the rod in the first channel.

20. The implantable device of claim 17, wherein the actuation device comprises:

a hinge, including:

a first arm having a first end portion pivotably coupled to a first support segment of the plurality of support segments;

a second arm having a first end portion pivotably coupled to a second support segment of the plurality of support segments; and a pivot portion pivotably coupling a second end portion of the first arm and a second end portion of the second arm; and an actuation mechanism coupled to the pivot portion, wherein, in response to an external force applied to the actuation mechanism that moves the pivot portion from a first vertical position to a second vertical position between the first support segment and the second support segment:

the first arm pivots in a first direction relative to the first support segment;

the second arm pivots in a second direction relative to the second support segment; and the first support segment and the second support segment move apart in response to the pivoting of the first arm in the first direction and the pivoting of the second arm in the second direction.

21. The implantable device of claim 17, wherein the actuation device comprises:

a hinge, including:

a first arm having a first end portion pivotably coupled to a first support segment and a second support segment of the plurality of support segments;

a second arm having a first end portion pivotably coupled to a third support segment and a fourth support segment of the plurality of support segments; and a pivot portion pivotably coupling a second end portion of the first arm and a second end portion of the second arm; and an actuation mechanism coupled to the pivot portion, wherein, in response to an external force applied to the actuation mechanism that moves the pivot portion from a first end portion of the plurality of support segments to an intermediate portion of the plurality of support segments, between the first end portion and a second end portion thereof:

the first arm moves in a first channel formed in the first support segment and a second channel formed in the second support segment, from the first end portion to the intermediate portion of the plurality of support segments;

the second arm moves in a third channel formed in the third support segment and a fourth channel formed in the fourth support segment, from the first end portion to the intermediate portion of the plurality of support segments; and in response to the movement of the first arm and the second arm, the first support segment and the second support segment move apart, and the third support segment and the fourth support segment move apart.

22. The implantable device of claim 17, wherein the actuation device comprises:

a threaded rod positioned between a first support segment and a second support segment of the plurality of support segments;

a first shim threadably coupled on a first portion of the threaded rod, the first shim contacting a first inclined surface of one of the first support segment or the second support segment; and a second shim threadably coupled on a second portion of the threaded rod, the second shim contacting a second inclined surface of one of the first support segment or the second support segment, wherein, in response to rotation of the threaded rod:

the first shim moves in a first direction along the first portion of the threaded rod, and in the first direction along the first inclined surface;

the second shim moves in a second direction along the second portion of the threaded rod, and in the second direction along the second inclined surface; and the first support segment and the second support segment move apart in response to the movement of the first shim along the first inclined surface and the movement of the second shim along the second inclined surface.

* * * * *